US011304902B2

(12) United States Patent
Pottier et al.

(10) Patent No.: US 11,304,902 B2
(45) Date of Patent: Apr. 19, 2022

(54) PHARMACEUTICAL COMPOSITIONS, PREPARATION AND USES THEREOF

(71) Applicant: CURADIGM SAS, Paris (FR)

(72) Inventors: Agnes Pottier, Paris (FR); Matthieu Germain, Champigny sur Marne (FR); Laurence Poul, Paris (FR); Marion Paolini, Neuilly sur Seine (FR); Marie-Edith Meyre, Saint Mande (FR)

(73) Assignee: CURADIGM SAS, Paris (FR)

( * ) Notice: Subject to any disclaimer, the term of this patent is extended or adjusted under 35 U.S.C. 154(b) by 26 days.

(21) Appl. No.: 15/529,097

(22) PCT Filed: Nov. 24, 2015

(86) PCT No.: PCT/EP2015/077441

§ 371 (c)(1),
(2) Date: May 24, 2017

(87) PCT Pub. No.: WO2016/083338

PCT Pub. Date: Jun. 2, 2016

(65) Prior Publication Data

US 2017/0258720 A1 Sep. 14, 2017

(30) Foreign Application Priority Data

Nov. 25, 2014 (EP) .................................... 14306876

(51) Int. Cl.
*A61K 9/127* (2006.01)
*A61K 9/51* (2006.01)
(Continued)

(52) U.S. Cl.
CPC .......... *A61K 9/1271* (2013.01); *A61K 9/0019* (2013.01); *A61K 9/0053* (2013.01);
(Continued)

(58) Field of Classification Search
CPC ................................ A61K 9/1271; A61K 9/51
See application file for complete search history.

(56) References Cited

U.S. PATENT DOCUMENTS 4,280,918 A 7/1981 Homola et al.
5,145,684 A * 9/1992 Liversidge ............. A61K 9/145 424/489

(Continued)

FOREIGN PATENT DOCUMENTS

CN 102532154 A * 7/2012
EP 2 000 150 12/2008

(Continued)

OTHER PUBLICATIONS

CC Ogu, JL Maza. "Drug Interactiosn Due to Cytochrome P450." BUMC Proceedings, vol. 13, 2000, pp. 421-423. (Year: 2000).*

(Continued)

*Primary Examiner* — Isaac Shomer
(74) *Attorney, Agent, or Firm* — Saliwanchik, Lloyd & Eisenschenk

(57) ABSTRACT

The present disclosure generally relates to the field of medicine. The present invention more specifically relates to a pharmaceutical composition comprising the combination of (i) at least one biocompatible nanoparticle comprising, or consisting in, at least one natural compound which is an inhibitor of a human CYP enzyme, the longest dimension of said nanoparticle being of at least 4 nm and less than 100 nm, and (ii) at least one compound of interest, typically at least one pharmaceutical compound, to be administered to a subject in need of such at least one compound of interest, wherein the combination of the at least one biocompatible nanoparticle and of the at least one compound of interest potentiates the at least one compound of interest's bioavailability. The at least one biocompatible nanoparticle is to be administered to the subject separately from the at least one (Continued)

compound of interest (preferably before), typically with an interval of between at least about 5 minutes (preferably more than about 5 minutes) and about 72 hours.

19 Claims, 8 Drawing Sheets

(51) Int. Cl.

| | |
|---|---|
| ***A61K 9/00*** | (2006.01) |
| ***A61K 31/37*** | (2006.01) |
| ***A61K 45/06*** | (2006.01) |
| ***C07D 491/14*** | (2006.01) |

(52) U.S. Cl.

CPC ................ *A61K 9/51* (2013.01); *A61K 9/513* (2013.01); *A61K 31/37* (2013.01); *A61K 45/06* (2013.01); *C07D 491/14* (2013.01); *A61K 2121/00* (2013.01)

(56) References Cited

U.S. PATENT DOCUMENTS

| | | | | | |
|---|---|---|---|---|---|
| 6,004,927 | A * | 12/1999 | Benet | A61K 38/13 514/1.2 |
| 6,054,490 | A * | 4/2000 | Sime | A61K 31/015 514/675 |
| 6,160,006 | A * | 12/2000 | Edwards | A61K 31/37 514/455 |
| 8,845,507 | B2 | 9/2014 | Levy et al. | |
| 2005/0090732 | A1 | 4/2005 | Ivkov et al. | |
| 2006/0264804 | A1 | 11/2006 | Karmon et al. | |
| 2007/0036834 | A1* | 2/2007 | Pauletti | A61K 9/0034 424/426 |
| 2008/0187595 | A1 | 8/2008 | Jordan et al. | |
| 2008/0193372 | A1* | 8/2008 | Lanza | A61K 9/1075 424/1.11 |
| 2009/0092661 | A1 | 4/2009 | Huang et al. | |
| 2011/0027375 | A1 | 2/2011 | Tillement et al. | |
| 2011/0152167 | A1* | 6/2011 | Hedrick | A61K 9/1075 514/1.1 |
| 2011/0213192 | A1 | 9/2011 | Levy et al. | |
| 2012/0157509 | A1* | 6/2012 | Hadwiger | C07K 5/1021 514/44 A |
| 2014/0056813 | A1 | 2/2014 | Pottier et al. | |
| 2014/0186447 | A1 | 7/2014 | Desai | |
| 2014/0271489 | A1 | 9/2014 | Grinstaff et al. | |
| 2015/0284353 | A1* | 10/2015 | Kim | A61K 31/365 549/299 |
| 2016/0184225 | A1 | 6/2016 | Pottier et al. | |
| 2016/0310614 | A1 | 10/2016 | Pottier et al. | |
| 2017/0258717 | A1 | 9/2017 | Germain et al. | |
| 2017/0258718 | A1 | 9/2017 | Meyre et al. | |
| 2017/0258721 | A1 | 9/2017 | Germain et al. | |
| 2017/0258937 | A1 | 9/2017 | Meyre et al. | |

FOREIGN PATENT DOCUMENTS

| | | | |
|---|---|---|---|
| EP | 2 537 530 | 12/2012 | |
| FR | 2 922 106 | 4/2009 | |
| JP | H10-120597 | 5/1998 | |
| JP | 2003-522143 | 7/2003 | |
| WO | WO 96/35415 | 11/1996 | |
| WO | WO-9908676 A1 * | 2/1999 | A61K 31/35 |
| WO | WO 01/58444 | 8/2001 | |
| WO | WO 2005/063305 | 7/2005 | |
| WO | WO 2005/086639 | 9/2005 | |
| WO | WO 2007/116954 | 10/2007 | |
| WO | WO 2007/128066 | 11/2007 | |
| WO | WO 2009/081287 | 7/2009 | |
| WO | WO 2009/105774 | 8/2009 | |
| WO | WO 2009/142754 | 11/2009 | |
| WO | WO 2009/147214 | 12/2009 | |
| WO | WO 2010/048623 | 4/2010 | |
| WO | WO 2011/070324 | 6/2011 | |
| WO | WO 2011/119988 | 9/2011 | |
| WO | WO 2011/151631 | 12/2011 | |
| WO | WO 2012/051220 | 4/2012 | |
| WO | WO 2012/104275 | 8/2012 | |
| WO | WO 2012/104277 | 8/2012 | |
| WO | WO 2014/039874 | 3/2014 | |
| WO | WO 2014/057432 | 4/2014 | |
| WO | WO 2014/191569 | 12/2014 | |
| WO | WO-2014191569 A1 * | 12/2014 | A61K 31/704 |
| WO | WO 2015/091888 | 6/2015 | |

OTHER PUBLICATIONS

RM Abra, ME Bosworth, CA Hunt. "Liposome Disposition in Vivo: Effects of Pre-Dosing with Liposomes." Research Communications in Chemical Pathology and Pharmacology, vol. 29 No. 2, Aug. 1980, pp. 349-360. (Year: 1980).*

English translation of CN 102532154 A. Obtained from Google Patents at https://patents.google.com/patent/CN102532154A/en?oq= CN 102532154+A on Oct. 23, 2018. 8 printed pages. Originally published in Chinese on Jan. 11, 2012. (Year: 2012).*

UChicago News. "Grapefruit juice boosts drug's anti-cancer effects. " Obtained from https://news.uchicago.edu/story/grapefruit-juice-boosts-drugs-anti-cancer-effects on Oct. 23, 2018. Originally published on Apr. 20, 2009. 4 printed pages. (Year: 2009).*

Y Uesawa, K Mohri. "Relationship Between Lipophilicities of 1,4-Dihydropyridine Derivatives and Pharmacokinetic Interaction Strengths with Grapefruit Juice." Yakugaku Zasshi—The Pharmaceutical Society of Japan. vol. 128(1), 2008, pp. 117-122. (Year: 2008).*

J Kiani, SZ Imam. "Medicinal importance of grapefruit juice and its interaction with various drugs." Nutrition Journal, vol. 6:33, 2007, pp. 1-9. (Year: 2007).*

T Ohta, T Maruyama, M Nagahashi, Y Miyamoto, S Hosoi, F Kiuchi, Y Yamazoe, S Tsukamoto. "Paradisin C: a new CYP3A4 inhibitor from grapefruit juice." Tetrahedron, vol. 58, 2002, pp. 6631-6635. (Year: 2002).*

W Tassaneeyakul, L-Q Guo, K Fukuda, T Ohta,, Y Yamazoe. "Inhibition Selectivity of Grapefruit Juice Components on Human Cytochromes P450." Archives of Biochemistry and Biophysics, vol. 378, No. 2, 2000, pp. 356-363. (Year: 2000).*

L-q Guo, Y Yamazoe. "Inhibition of Cytochrome P450 by furanocoumarins in grapefruit juice and herbal medicines." Acta Pharmacologica Sinica, vol. 25(2), Feb. 2004, pp. 129-136. (Year: 2004).*

Theunis C. Goosen et al. "Bergamottin contribution to the grapefruit juice-felodipine interaction and disposition in humans." Clinical Pharmacology and Therapeutics, vol. 76, 2004, pp. 607-617. (Year: 2004).*

Teemu Kantola, Kari T. Kivisto, and Pertti J. Neuvonen. "Grapefruit juice greatly increases serum concentrations of lovastatin and lovastatin acid." Clinical Pharmacology and Therapeutics, vol. 63 No. 4, 1998, pp. 397-402. (Year: 1998).*

H Yamazaki and T Shimada. "Effects of arachidonic acid, prostaglandins, retinol, retinoic acid and cholecalciferol on xenobiotic oxidations catalysed by human cytochrome P450 enzymes." Xenobiotica, vol. 29 No. 3, 1999, pp. 231-241. (Year: 1999).*

Casetext.com "Application of Greenfield." https://casetext.com/case/application-of-greenfield?q= accessed Aug. 4, 2021, originally published Mar. 16, 1978, 9 printed pages. (Year: 1978).*

Casetext.com "Application of Coleman." https://casetext.com/case/application-of-kollman accessed Aug. 5, 2021, originally published Mar. 15, 1979, 16 printed pages. (Year: 1979).*

Elizabeth Landrum Michalets. "Update: Clinically Significant Cytochrome P-450 Drug Interactions." Pharmacotherapy, vol. 18, No. 1, 1998, pp. 84-112. (Year: 1998).*

Babcock, J. J. et al. "Bovine serum albumin oligomers in the E- and B-forms at low protein concentration and ionic strength" *International Journal of Biological Macromolecules*, Feb. 1, 2013, pp. 42-53, vol. 53.

(56) References Cited

OTHER PUBLICATIONS

Ma, P. et al. "Paclitaxel Nano-Delivery Systems: A Comprehensive Review" *Journal of Nanomedicine and Nanotechnology*, Jan. 1, 2013, pp. 1-16, vol. 4, No. 2.
Written Opinion in International Application No. PCT/EP2015/077423, dated Jan. 21, 2016, pp. 1-5.
He, C. et al. "Effects of particle size and surface charge on cellular uptake and biodistribution of polymeric nanoparticles" *Biomaterials*, May 1, 2010, pp. 3657-3666, vol. 31, No. 13.
"NCL Method PCC-2 Measuring Zeta Potential of Nanoparticles" Nov. 1, 2009, Retrieved from the Internet: URL:http://ncl.cancer.gov/NCL_Method_PCC-2.pdf on Feb. 23, 2015, pp. 1-14.
Written Opinion in International Application No. PCT/EP2015/077446, dated Feb. 3, 2016, pp. 1-6.
Banquy, X. et al. "Effect of mechanical properties of hydrogel nanoparticles on macrophage cell uptake" *Soft Matter*, Jan. 1, 2009, pp. 3984-3991, vol. 5, No. 20.
Written Opinion in International Application No. PCT/EP2015/077438, dated Jan. 27, 2016, pp. 1-7.
Written Opinion in International Application No. PCT/EP2015/077425, dated Jan. 15, 2016, pp. 1-6.
Abu Lila, A. S. et al. "Oxaliplatin encapsulated in PEG-coated cationic liposomes induces significant tumor growth suppression via a dual-targeting approach in a murine solid tumor model" *Journal of Controlled Release*, 2009, pp. 8-14, vol. 137.
Gabizon, A. A. "Liposome circulation time and tumor targeting: implications for cancer chemotherapy"*Advanced Drug Delivery Reviews*, 1995, pp. 285-294, vol. 16.
Harashima, H. et al. "Size Dependent Liposome Degradation in Blood: In Vivo/In Vitro Correlation by Kinetic Modeling" *Journal of Drug Targeting*, 1995, pp. 253-261, vol. 3.
Hadaruga, D. I. et al. "Liposomes containing titanium dioxide nanoparticles (Short communication)" *Journal of Agroalimentary Processes and Technologies*, 2010, pp. 62-66, vol. 16, No. 1.
Shamsipour, F. et al. "Conjugation of Monoclonal Antibodies to Super Paramagnetic Iron Oxide Nanoparticles for Detection of her2/neu Antigen on Breast Cancer Cell Lines" *Journal of Medical Biotechnology*, Apr.-Jun. 2009, pp. 27-31, vol. 1, No. 1.
Kim, J-Y. et al. "In-vivo tumor targeting of pluronic-based nano-carriers" *Journal of Controlled Release*, 2010, pp. 109-117, vol. 147.
Yu, M. K. et al. "Drug-Loaded Superparamagnetic Iron Oxide Nanoparticles for Combined Cancer Imaging and Therapy In Vivo" *Angew. Chem. Int. Ed.*, 2008, pp. 5362-5365, vol. 47.
Choi, W. I. et al. "The effect of mechanical properties of iron oxide nanoparticle-loaded functional nano-carrier on tumor targeting and imaging" *Journal of Controlled Release*, 2012, pp. 267-275, vol. 162.
Liang, X. et al. "Mechanical properties and stability measurement of cholesterol-containing liposome on mica by atomic force microscopy" Journal of Colloid and Interface Science, 2004, pp. 53-62, vol. 278.
Nie, Y. et al. "Cholesterol Derivatives Based Charged Liposomes for Doxorubicin Delivery: Preparation, In Vitro and In Vivo Characterization" *Theranostics*, 2012, pp. 1092-1103, vol. 2, No. 11.
Bhatt, N. et al. "Stability study of O/W emulsions using zeta potential" *Journal of Chemical and Pharmaceutical Research*, 2010, pp. 512-527, vol. 2, No. 1.
Yu, S. et al. "Carboxyl group ($-CO_2H$) functionalized ferrimagnetic iron oxide nanoparticles for potential bio-applications" *Journal of Materials Chemistry*, 2004, pp. 2781-2786, vol. 14.
Ismail, M.F. et al. "Potential therapeutic effect of nanobased formulation of rivastigmine on rat model of Alzheimer's disease" *International Journal of Nanomedicine*, 2013, pp. 393-406, vol. 8.
Bowen, P., "Particle Size Distribution Measurement from Millimeters to Nanometers and from Rods to Platelets," *Journal of Dispersion Science and Technology*, Jan. 1, 2002, vol. 23, No. 5, pp. 631-662.
Written Opinion in International Application No. PCT/EP2014/061296, dated Sep. 5, 2014, pp. 1-9.
Thongborisute, J. et al. "Properties of Liposomes coated with hydrophobically modified chitosan in oral liposomal drug delivery" *Pharmazie*, 2006, pp. 106-111, vol. 61.
Olson, F. et al. "Preparation of Liposomes of Defined Size Distribution by Extrusion Through Polycarbonate Membranes" *Biochimica et Biophysica Acta*, 1979, pp. 9-23, vol. 557.
Lu, H. et al. "Drug-target residence time: critical information for lead optimization" *Current Opinion in Chemical Biology*, 2010, pp. 467-474, vol. 14.
Copeland, R. A. et al. "Drug-target residence time and its implications for lead optimization" *Nature Reviews/Drug Discovery*, Sep. 2006, pp. 730-739, Corrigendum (1 page), vol. 5.
Simoes, S. et al. "Cationic liposomes for gene delivery" *Expert Opinion in Drug Delivery*, 2005, pp. 237-254, vol. 2, No. 2.
Singh, R. et al. "Nanoparticle-based targeted drug delivery" *Experimental and Molecular Pathology*, 2009, pp. 215-223, vol. 86.
Lai, B.-H. et al. "Surface modification of iron oxide nanoparticles with polyarginine as a highly positively charged magnetic nano-adsorbent for fast and effective recovery of acid proteins" *Process Biochemistry*, 2012, pp. 799-805, vol. 47.
Dekrafft, K.E. et al. "Zr- and Hf-based nanoscale metal-organic frameworks as contrast agents for computed tomography" *Journal of Materials Chemistry*, Sep. 21, 2012, pp. 18139-18144, vol. 22, No. 35.
Maggiorella, L. et al. "Nanoscale radiotherapy with hafnium oxide nanoparticles" *Future Oncology*, Sep. 1, 2012, pp. 1167-1181, vol. 8, No. 9.
Written Opinion in International Application No. PCT/EP2014/078619, dated Mar. 26, 2015, pp. 1-6.
Belisario, M. A. et al. "Effect of avarol, avarone and nine of their natural and synthetic derivatives on microsomal drug-metabolizing enzymes" *Toxicology Letters*, 1991, pp. 183-193, vol. 57.
Michalets, E. L. et al. "Update: Clinically Significant Cytochrome P-450 Drug Interactions" *Pharmacotherapy*, 1998, pp. 84-112, vol. 18, No. 1.
Written Opinion in International Application No. PCT/EP2015/077441, dated Feb. 3, 2016, pp. 1-6.
Harvey, V. et al. "Phase III Trial Comparing Three Doses of Docetaxel for Second-Line Treatment of Advanced Breast Cancer" *Journal of Clinical Oncology*, Nov. 1, 2006, pp. 4963-4970 and p. 5790, vol. 24, No. 31.
Vandermolen, K. M. et al. "Rapid Quantitation of Furanocoumarins and Flavonoids in Grapefruit Juice using Ultra Performance Liquid Chromatography" *Phytochem Anal.*, 2013, pp. 1-15, vol. 24, No. 6.
Yong, S.-B. et al. "Mononuclear phagocytes as a target, not a barrier, for drug delivery" *Journal of Controlled Release*, 2017, pp. 53-61, vol. 259.
Ekroos, M. et al. "Structural basis for ligand promiscuity in cytochrome P450 3A4" *PNAS*, Sep. 12, 2006, pp. 13682-13687, vol. 103, No. 37.
Olguin-Reyes, S. et al. "Bergamottin is a competitive inhibitor of CYP1A1 and is antimutagenic in the Ames test" *Food and Chemical Toxicology*, 2012, pp. 3094-3099, vol. 50.
Nakanishi, K. et al. "Progesterone Hydroxylation by Cytochromes P450 2C and 3A Enzymes in Marmoset Liver Microsomes" *Xenobiotica*, 2017, DOI: 10.1080/00498254.2017.1363444, pp. 1-23.
Ohkura, K. et al. "Flexible Structure of Cytochrome P450: Promiscuity of Ligand Binding in The CYP3A4 Heme Pocket" *Anticancer Research*, 2009, pp. 935-942, vol. 29.
Harlow, G. R. et al. "Analysis of human cytochrome P450 3A4 cooperativity: Construction and characterization of a site-directed mutant that displays hyperbolic steroid hydroxylation kinetics" *Proc. Natl. Acad. Sci. USA*, Jun. 1998, pp. 6636-6641, vol. 95.
Aperis, G. et al. "Tolvaptan: A New Therapeutic Agent" *Reviews on Recent Clinical Trials*, 2011, pp. 177-188, vol. 6, No. 2.
Bart, A. G. et al. "Structures of human cytochrome P450 1A1 with bergamottin and erlotinib reveal active-site modifications for binding of diverse ligands" *J. Biol. Chem*, 2018, pp. 19201-19210, vol. 293, No. 50.
Bai, J. et al. "Heterotropic activation of flavonoids on cytochrome P450 3A4: a case example of alleviating dronedarone-induced cytotoxicity" *Toxicology Letters*, 2019, DOI: https:/doi.org/10.1016/j.toxlet.2019.11.016, pp. 1-37.

(56) References Cited

OTHER PUBLICATIONS

Berger, B. et al. "Cytochrome P450 Enzymes Involved in Metoprolol Metabolism and Use of Metoprolol as a CYP2D6 Phenotyping Probe Drug" *Frontiers in Pharmacology*, Jul. 24, 2018, pp. 1-11, vol. 9, Article 774.
Boni, J. et al. "Disposition of desipramine, a sensitive cytochrome P450 2D6 substrate, when coadministered with intravenous temsirolimus" *Cancer Chemother Pharmacol*, 2009, pp. 263-270, vol. 64.
Boyce, E. G. et al. "Sildenafil Citrate: A Therapeutic Update" *Clinical Therapeutics*, 2001, pp. 2-23, vol. 23, No. 1.
Byeon, J.-Y. et al. "Influence of CYP2D6 genetic polymorphism on pharmacokinetics of active moiety of tolterodine" Dec. 12, 2018, *Arch. Pharm. Res.*, pp. 1-9.
Chen, L. et al. "Validation of a Sensitive UHPLC-MS/MS Method for Cytochrome P450 Probe Substrates Caffeine, Tolbutamide, Dextromethorphan, and Alprazolam in Human Serum Reveals Drug Contamination of Serum Used in Research" *Journal of Pharmaceutical and Biomedical Analysis*, 2019, doi: https://doi.org/10.1016/jjpba.2019.112983, pp. 1-35.
Chiu, Y.-Y. et al. "Lurasidone drug-drug interaction studies: a comprehensive review" *Drug Metab Drug Interact*, 2014, pp. 191-202, vol. 29, No. 3.
Cvetkovic, R. S. et al. "Lopinavir/Ritonavir, A Review of its Use in the Management of HIV Infection" *Drugs*, 2003, pp. 769-802, vol. 63, No. 8.
DeVane, C. L. et al. "Clinical Pharmacokinetics of Quetiapine" *Clin Pharmacokinet*, 2001, pp. 509-522, vol. 40, No. 7.
D'Souza, D. L. et al. "Effect of Alosetron on the Pharmacokinetics of Fluoxetine" *Journal of Clinical Pharmacology*, 2001, pp. 455-458, vol. 41.
Dresser, G. K. et al. "Pharmacokinetic-Pharmacodynamic Consequences and Clinical Relevance of Cytochrome P450 3A4 Inhibition" *Clin Pharmacokinet*, Jan. 2000, pp. 41-57, vol. 38, No. 1.
Fujita, K.-I. "Food-Drug Interactions Via Human Cytochrome P450 3A (CYP3A)" 2004, pp. 195-217, vol. 20, No. 4.
Günes, S. et al. "Spontaneous Spinal Epidural Hematoma During Simultaneous Tocilizumab and Warfarin Use in a Patient With Rheumatoid Arthritis: Is There a Drug Interacton Between Tocilizumab and Oral Anticoagulants?" *Arch Rheumatol*, 2020, pp. 614-617, vol. 35, vol. 4.
Guo, L. et al. "Influence of CYP2D6*5 and *10 polymorphism on the pharmacokinetics of nebivolol in healthy Chinese subjects" *Journal of Clinical Pharmacy and Therapeutics*, 2020, https://doi.org/10.111/jcpt.13155, pp. 1-6.
Hirota, T. et al. "An updated review of pharmacokinetic drug interactions and pharmacogenetics of statins" *Expert Opinion on Drug Metabolism & Toxicology*, 2020, DOI: 10.1080/17425255.2020.1801634, pp. 1-41.
Kanacher, T. et al. "A Physiologically-Based Pharmacokinetic (PBPK) Model Network for the Prediction of CYP1A2 and CYP2C19 Drug-Drug-Gene Interactions with Fluvoxamine, Omeprazole, S-mephenytoin, Moclobemide, Tizanidine, Mexiletine, Ethinylestradiol, and Caffeine" *Pharmaceutics*, 2020, p. 1-15, vol. 12, No. 1191.
Kirchner, G. I. et al. "Clinical Pharmacokinetics of Everolimus" *Clin Pharmacokinet*, 2004, pp. 83-95, vol. 43, No. 2.
Leveque, D. et al. "Clinical Pharmacokinetics and Pharmacodynamics of Dasatinib" *Clinical Pharmacokinetics*, Feb. 29, 2020, pp. 1-8.
Li, C. et al. "Effects of myricetin, an anticancer compound, on the bioavailability and pharmacokinetics of tamoxifen and its main metabolite, 4-hydroxytamoxifen, in rats" *Eur J Drug Metab Pharmacokinet*, 2011, pp. 175-182, vol. 36.
Li, X. et al. "A Physiologically Based Pharmacokinetic Model of Voriconazole Integrating Time-Dependent Inhibition of CYP34A, Genetic Polymorphisms of CYP2C19 and Predictions of Drug-Drug Interactions" *Clinical Pharmacokinetics*, Dec. 19, 2019, pp. 1-28.
Li-Ng, M. "Conivaptan: Evidence supporting its therapeutic use in hyponatremia" *Core Evidence*, Jun. 24, 2009, pp. 83-92, vol. 4.
Madden, S. et al. "Clinical Pharmacokinetics of Tacrine" *Clin Pharmacokinet*, 1995, pp. 449-457, vol. 28, No. 6.
Mahalati, K. et al. "Clinical Pharmacokinetics of Sirolimus" *Clin Pharmacokinet*, 2001, pp. 573-585, vol. 40, No. 8.
Martin, C. S. et al. "Iatrogenic Cushing's syndrome related to the interaction between oral budesonide with fluvoxamine: a case report" *Journal of Clinical Pharmacy and Therapeutics*, 2015, pp. 612-614, vol. 40.
McGraw, J. et al. "The relative role of CYP3A4 and CYP3A5 in eplerenone metabolism" *Toxicology Letters*, 2019, pp. 9-13, vol. 315.
Molto, J. et al. "Interacciones medicamentosas de darunavir" *Enferm Infecc Microbiol Clin.*, 2008, pp. 43-50, vol. 26, Supl 10.
Notsu, Y. et al. "Simple pharmacokinetic models accounting for drug monitoring results of atomoxetine and its 4-hydroxylated metabolites in Japanese pediatric patients genotyped for cytochrome P450 2D6" *Drug Metabolism and Pharmacokinetics*, 2019, https://doi.org/10.1016/j.dmpk.2019.08.005, pp. 1-10.
Obach, R. S. et al. "Metabolism of Ramelteon in Human Liver Microsomes and Correlation with the Effect of Fluvoxamine on Ramelteon Pharmacokinetics" *Drug Metabolism and Disposition*, 2010, pp. 1381-1391, vol. 38, No. 8.
Peng, B. et al. "Clinical Pharmacokinetics of Imatinib" *Clin Pharmacokinet*, 2005, pp. 879-894, vol. 44, No. 9.
Sanchez, R. I. et al. "Cytochrome P450 3A4 is the Major Enzyme Involved in the Metabolism of the Substance P Receptor Antagonist Aprepitant" *Drug Metabolism and Disposition*, 2004, pp. 1287-1292, vol. 32, No. 11.
Skerjanec, A. "The Clinical Pharmacokinetics of Darifenacin" *Clin Pharmacokinet*, 2006, pp. 325-350, vol. 45, No. 4.
Suwata, J. et al. "Venlafaxine pharmacogenetics: a comprehensive review" *Pharmacogenomics*, 2019, pp. 1-18.
Takiya, L. et al. "Safety and Efficacy of Eletriptan in the Treatment of Acute Migraine" *Pharmacotherapy*, 2006, pp. 115-128, vol. 26, No. 1.
Tan, C. R. C. et al. "Clinical Pharmacokinetics and Pharmacodynamics of Bortezomib" *Clin Pharmacokinet*, May 26, 2018, pp. 1-12.
Van Eijk, M. et al. "Cytochrome P450 3A4, 3A5, and 2C8 expression in breast, prostate, lung, endometrial, and ovarian tumors: relevance for resistance to taxanes" *Cancer Chemotherapy and Pharmacology*, 2019, pp. 487-499, vol. 84.
Waade, R. B. et al. "Impact of CYP2D6 on serum concentrations of flupentixol, haloperidol, perphenazine and zuclopenthixol" 2020, doi: 10.1111/bcp.14626, pp. 1-20.
Weissenstein, U. et al. "Absence of herb-drug interactions of mistletoe with the tamoxifen metabolite (E/Z)-endoxifen and cytochrome P450 3A4/5 and 2D6 in vitro" *BMC Complementary and Alternative Medicine*, 2019, pp. 1-12, vol. 19, No. 23.
Yang, S. H. et al. "Effects of morin on the pharmacokinetics of etoposide in 7,12-dimethylbenz[a]anthracene-induced mammary tumors in female Sprague-Dawley rats" *Oncology Reports*, 2013, pp. 1215-1223, vol. 29.
Yost, R. et al. "Maraviroc: A coreceptor CCR5 antagonist for management of HIV infection" *Am J Health-Syst Pharm.*, Apr. 15, 2009, pp. 715-726, vol. 66.
Zhou, S. et al. "Pharmacokinetic interactions of drugs with St John's wort" *Journal of Psychopharmacology*, 2004, pp. 262-276, vol. 18, No. 2.
Zhu, M. et al. "Cytochrome P450 3A-Mediated Metabolism of Buspirone in Human Liver Microsomes" *Drug Metabolism and Disposition*, 2005, pp. 500-507, vol. 33, No. 4.
Diao, L. et al. "CD44-targeted hyaluronic acid-curcumin reverses chemotherapeutics resistance by inhibiting P-gp and anti-apoptotic pathways" *RSC Advances*, 2019, pp. 40873-40882, vol. 9.
Fontana, E. et al. "Cytochrome P450 Enzymes Mechanism Based Inhibitors: Common Sub-Structures and Reactivity" *Current Drug Metabolism*, 2005, pp. 413-454, vol. 6, No. 5.
Raposo, C. D. et al. "Development of Novel Galactosylated PLGA Nanoparticles for Hepatocyte Targeting Using Molecular Modelling" *Polymers*, Jan. 4, 2020, pp. 1-18, vol. 12, No. 94.
Sevrioukova, I. F. "Structural Insights into the Interaction of Cytochrome P450 3A4 with Suicide Substrates: Mibefradil, Azamulin and 6',7'-Dihydroxybergamottin" *International Journal of Molecular Sciences*, Aug. 30, 2019, pp. 1-11, vol. 20, No. 4245.

(56) References Cited

OTHER PUBLICATIONS

Zhou, S. et al. "Mechanism-Based Inhibition of Cytochrome P450 3A4 by Therapeutic Drugs" *Clin Pharmacokinet*, 2005, pp. 279-304, vol. 44, No. 3.

* cited by examiner

6′,7′-dihydroxybergamottin (DHB)

6′,7′-epoxybergamottin

Bergamottin

Paradisin A

PHARMACEUTICAL COMPOSITIONS, PREPARATION AND USES THEREOF

CROSS-REFERENCE TO RELATED APPLICATION

This application is the U.S. national stage application of International Patent Application No. PCT/EP2015/077441, filed Nov. 24, 2015.

FIELD OF THE INVENTION

The present disclosure generally relates to the field of medicine. The present invention more specifically relates to a pharmaceutical composition comprising the combination of (i) at least one biocompatible nanoparticle comprising, or consisting in, at least one natural compound, typically at least one natural compound which is an inhibitor of a human CYP enzyme, such as furanocoumarin, or a synthetic analog thereof, the longest dimension of said nanoparticle being of at least 4 nm and less than 100 nm, and of (ii) at least one compound of interest, typically at least one pharmaceutical compound, to be administered to a subject in need of such at least one compound of interest, wherein the combination of the at least one biocompatible nanoparticle and of the at least one compound of interest potentiates the at least one compound of interest's bioavailability. Preferably, the at least one biocompatible nanoparticle is not used as such as a therapeutic or prophylactic compound.

The at least one biocompatible nanoparticle is to be administered to the subject separately from the at least one compound of interest (preferably before), typically with an interval of between at least about 5 minutes (preferably more than about 5 minutes) and about 72 hours.

The present disclosure further relates to uses of this pharmaceutical composition in the therapeutic area. The pharmaceutical composition of the invention typically allows a reduction of at least about 20% of the administered compound(s) pharmaceutical dose(s) when compared to the standard pharmaceutical dose of each of said pharmaceutical compound(s).

BACKGROUND

In order to ensure safety and efficacy, therapeutic compounds are required to be selectively delivered to their target site at an optimal rate in the subject in need thereof.

Pharmacokinetics (pK) is a branch of pharmacology dedicated to the determination of the fate of substances administered externally to a living organism. This determination involves steps of measuring compound's concentrations in all major tissues over a long enough period of time, preferably until the compound's elimination. Pharmacokinetics is necessary to efficiently describe the compound's behavior in vivo, including the mechanisms of its absorption and distribution as well as its chemical changes in the organism. The pK profile in the blood can be fitted using various programs to obtain key pK parameters that quantitatively describe how the body handles the compound. Important parameters include maximum concentration ($C_{max}$), half-life ($t_{1/2}$), clearance, area under curve (AUC), and mean resident time (MRT), i.e. the average time during which a compound stays in an organism. pK data are often used in deciding the optimal dose and dose regimen for maintaining the desirable blood concentration in order to improve therapeutics' efficiency with minimal side effects. In addition, as well known by the skilled person, the blood concentration of a compound is correlated with both its efficacy and toxicity in most cases, typically for free drugs.

Differences in drug response among patients are common, often leading to challenges in optimizing dosage regimen for an individual patient. Most major drugs are effective in only 25 to 60 percent of patients, and more than 2 million cases of adverse drug reactions occur annually in the United States, including 100,000 deaths [Drug metabolism and variability among patients in drug response. Wilkinson G R. The New England Journal of Medicine. 352;21 May 26, 2005, 2211-21]. Such variability in drug response among patients is multifactorial, including environmental, genetic, and disease determinants that affect the disposition (absorption, distribution, metabolism, and excretion) of a given drug. The interplay of these factors determines the profile of the plasma concentration over time for a drug and, therefore, its elicited pharmacologic effect at the site of interaction with targets.

Cytochrome P-450 enzymes (CYPs) are a family of enzymes expressed in the liver and the intestines. They metabolize many chemicals present in the diet and environment, as well as medications. Cytochrome P-450 enzymes reduce or alter the pharmacologic activity of many drugs and facilitate their elimination.

The liver is the major site of cytochrome P-450-mediated metabolism, but the enterocytes in the epithelium of the small intestine are also a potentially important site. Thus after oral administration of a drug, cytochrome P-450 enzymes located in the intestine and in the liver may reduce the portion of dose that reaches the systemic circulation (i.e. the bioavailability) and, subsequently, may influence the drug effect/efficiency—a phenomenon termed first-pass metabolism.

Furthermore, drug interactions resulting in either inhibition or induction of the involved enzymes can markedly alter bioavailability. CYP3A is probably the most important of all drug-metabolizing enzymes because of its abundance in both the intestinal epithelium and the liver. Drug interactions may inhibit or reduce CYP3A activity or may on the contrary induce or increase CYP3A metabolic activity. Such interactions can expand the range of variability of blood drug levels to about 400-fold. This variability in drug levels, if not recognized and understood, potentially presents a major therapeutic problem in dosage optimization.

There is a long unresolved need to enhance the bioavailability of drug(s) (i.e. to reduce the first-pass metabolism of drug(s)), while maintaining, preferably while reducing, the administered dose(s) to the patient. There is also a long unresolved need to reduce the variability of blood drug levels in order to optimize dosage regimen for an individual patient.

DETAILED DESCRIPTION

The present invention now allows optimization of the bioavailability of a compound of interest (herein also simply identified as "the compound") or of a combination of several compounds of interest, whatever its/their intended use(s) in the context of therapy and/or prophylaxis. The composition herein described, which is a combination of (i) at least one biocompatible nanoparticle and of (ii) at least one compound of interest, typically of at least one pharmaceutical compound, optimizes the bioavailability of the at least one compound of interest in a subject. Preferably, the at least one biocompatible nanoparticle is not used as such as a therapeutic or prophylactic compound. The dose(s) of compound (s) of interest required to get a therapeutic and/or prophylactic effect(s) in a subject are thus reduced, thereby improving the health-related quality of life of said subject. Typically, the ratio between the (at least one) biocompatible nanoparticles and compounds of interest is between 0.1/1 and 1000/1 or 0.5/1 and 1000/1, preferably between 0.5/1 and 500/1, even more preferably between 0.5/1 and 300/1. The present invention also reduces costs associated with diseases with high economic impact.

The at least one biocompatible nanoparticle typically comprises, or consists in, at least one natural compound (i.e. found in nature) which is an inhibitor of a human CYP enzyme, typically at least one compound preferably selected from a furanocoumarin (such as bergamottin, 6',7'-dihydroxybergamottin (DHB), 6',7'-epoxybergamottin, bergaptol, paradisin A, paradisin B, or paradisin C), a flavonoid (such as acacetin, naringenin, apigenin or quercetin), a fatty acid (such as arachidonic acid), a vitamin (such as vitamin A, in particular retinol). Also included in the present invention are synthetic (artificial) compounds identical to the compounds found in nature. The longest dimension of the at least one biocompatible nanoparticle is typically between at least 4 nm and less than 100 nm.

The terms "about" and "around" when associated to a value such as for example a nanoparticle' size or a time interval indicates that a variation with the indicated value, which would be recognized by the skilled person as small variation, does not substantially impact the properties of the subject-matter it is associated to and that said subject-matter remains in the spirit of the claimed invention.

A typical composition of the invention (herein generally identified as "pharmaceutical composition") is a composition comprising the combination of (i) at least one biocompatible nanoparticle comprising, or consisting in, at least one natural compound which is an inhibitor of a human CYP enzyme or a synthetic version or analog thereof, the longest dimension of said nanoparticle being of at least 4 nm and below 100 nm, and of (ii) at least one compound of interest, typically of at least one pharmaceutical compound. The pharmaceutical composition of the invention is for use for administering the at least one compound of interest in a subject in need thereof. In the context of the present invention, the at least one nanoparticle and the at least one compound ("compound of interest") are advantageously to be administered sequentially to the subject in need of said at least one compound of interest, typically between at least (or more than) about 5 minutes and about 72 hours one from each other, preferably between at least (or more than) about 5 hours and about 72 hours, even more preferably between at least (or more than) about 5 hours and about 24 hours, in order to optimize the compound pharmaceutical efficacy. Preferably, the nanoparticle(s) is/are administered before the compound of interest.

The present description also concerns a composition as previously described comprising, in addition to the "first" at least one biocompatible nanoparticle, a "second" biocompatible nanoparticle. This "second" biocompatible nanoparticle also comprises, or consists in, at least one natural compound or a synthetic analog thereof. The longest dimension of this "second" biocompatible nanoparticle is typically between at least 4 nm and less than 100 nm.

This "second" biocompatible nanoparticle can be identical to, or different from, the "first" biocompatible nanoparticle. When identical, they are preferably administered sequentially to a given subject and/or administered through different routes to said subject. When different, they can be administered simultaneously or sequentially to a given subject and through an identical or a different route.

The at least "first" and "second" biocompatible nanoparticles are administered separately or simultaneously in a subject in need of the at least one pharmaceutical compound, and preferably before the at least one pharmaceutical compound. Typically, the at least "first" and "second" biocompatible nanoparticles are administered between at least about 5 minutes, preferably more than about 5 minutes, and about 72 hours before the pharmaceutical compound(s), preferably between more than 5 hours and about 72 hours before the pharmaceutical compound(s).

In a particular embodiment, the at least one biocompatible nanoparticle comprising, or consisting in, at least one natural compound or a synthetic analog thereof, and the at least one pharmaceutical compound are both administered to the subject through the same route which is typically an intravenous (IV) route, a subcutaneous route, an oral route, or an enteral route.

In a preferred embodiment, only one of the "first" and "second" biocompatible nanoparticles is administered to the subject through the same route as the compound of interest which is an oral or enteral route, the remaining "first" or "second" biocompatible nanoparticle being advantageously administered through a different route which is selected from a IV, subcutaneous, oral or enteral route.

The selected size of the nanoparticles allows for their efficient cell uptake. In addition, when IV or subcutaneously administered to the subject in need thereof, the selected size of the nanoparticles allows for their extravasation into the liver organ. Therefore, by sequentially administering the biocompatible nanoparticles of the invention and the compound(s) of interest, no co-circulation or a limited co-circulation of the two compounds (i.e. of the biocompatible nanoparticle and of the compound(s) of interest), is achieved. Therefore, the size of the biocompatible nanoparticles permits the safe use of the compound(s) of interest whereas the dose(s) of compound(s) of interest required to get a therapeutic and/or prophylactic effect(s) in a subject is(are) thus reduced, thereby improving the health-related quality of life of said subject and reducing costs associated with diseases with high economic impact.

The biocompatible nanoparticle typically comprises, or consists in, at least one natural compound which is an inhibitor of a human CYP enzyme or a synthetic analog thereof.

When the biocompatible nanoparticle (the at least one biocompatible nanoparticle or any additional biocompatible nanoparticle) comprises, or consists in, at least one natural compound, the natural compound can typically be selected from a flavonoid (such as acacetin, naringenin, apigenin or quercetin), a furanocoumarin, a fatty acid (such as arachidonic acid), and a vitamin (such as vitamin A, in particular retinol). Also included in the present invention are synthetic (or artificial) compounds identical to the previously identified compounds which can be found in nature (herein also identified as "natural compounds" or "natural products").

In a preferred embodiment, the at least one biocompatible nanoparticle typically comprises, or consists in, at least one furanocoumarin or a synthetic analog thereof.

In the context of the present invention, the term "furanocoumarin" designates a furanocoumarin monomer, dimer, trimer or oligomer as well as a mixture thereof (cf. FIG. 1).

In a particular embodiment, the at least one biocompatible nanoparticle consists in at least two, preferably more than 10, 15 or 20 furanocoumarins (or a synthetic analog thereof) monomers or dimers.

The at least one furanocoumarin of the "first" and/or "second" biocompatible nanoparticle(s) is thus typically a furanocoumarin monomer, dimer or oligomer.

When furanocoumarin is a monomer, it can be for instance selected from bergamottin, 6',7'-dihydroxybergamottin (DHB), 6',7'-epoxybergamottin, bergaptol and any mixture thereof. When furanocoumarin is a dimer, it can be for instance paradisin such as paradisin A, paradisin B, or paradisin C.

So long as it comprises a natural compound which is an inhibitor of a human CYP enzyme, for example at least one furanocoumarin or flavonoid, the nanoparticle used in the context of the invention can be either organic or inorganic. A mixture of organic and inorganic nanoparticles can further be used.

The natural compound which is an inhibitor of a human CYP enzyme, for example furanocoumarin(s) or flavonoid (s), can be encapsulated in, trapped in, absorbed in, adsorbed on, linked on, conjugated to, attached to or bound to the biocompatible nanoparticle(s). The interaction between the nanoparticle and the natural compound which is an inhibitor of a human CYP enzyme can be performed by hydrogen bonding, electrostatic interactions, complexation, covalent linking or hydrophobic interaction. Direct interactions between the nanoparticle and the natural compound which is an inhibitor of a human CYP enzyme can be achieved or a linker may be used.

When organic, the nanoparticle can be a lipid-based nanoparticle (glycerolipid, phospholipid, sterol lipid, etc.), such as a solid-lipid nanoparticle, a protein-based nanoparticle also herein identified as "protein-nanoparticle" (albumin for instance), a polymer-based nanoparticle ("polymeric nanoparticle"), a co-polymer-based nanoparticle ("co-polymeric nanoparticle"), a carbon-based nanoparticle, a virus-like nanoparticle (for example a viral vector).

The organic nanoparticle may further be a nanosphere (plain nanoparticle) or a nanocapsule (hollow nanoparticle) such as a liposome, a gel, a hydrogel, a micelle, a dendrimer, etc. A mixture of the herein described organic nanoparticles can also be used.

The polymer or co-polymer can be of natural or synthetic origin.

Examples of synthetic (artificial) and natural polymers or co-polymers usable in the context of the invention to prepare organic nanoparticles can be selected from polylactic acid (PLA), Poly (lactide-co-glycolic) acid (PLGA), Polyethyleneglycol (PEG), Polyglactin, Polylactide, Polyoxyethylene fatty acid esters, Polypropylene glycol, Polysorbate (such as polysorbate 20 or polysorbate 80), Cremophor EL, Polyvinyl alcohol, Polystyrene, Polyacrylamide, Polyalkylmethacrylate, Polyalkylcyanoacrylate, Polylactateco-glycolate, Poly(amido amine), Poly(ethyleneimine), Poly(ε-caprolactone) (PCL), Poly(vinylpyridine), alginate, chitosan, cellulose and cellulose derivatives polymers, collagen, hyaluronic acid, polyglutamic acid (PGA), actin, polysaccharide, and gelatin. The organic nanoparticle can also be a cyclodextrin nanoparticle.

When inorganic and when its longest dimension is typically below about 10 nm, for example below about 8 nm, below about 7 nm, typically comprised between about 7 nm and about 4 nm, for example below about 6 nm, below about 5 nm or below about 4 nm, the nanoparticle may be made of any inorganic material. The inorganic material may for example comprise metallic element from period 3, 4, 5, 6 of the Mendeleev's periodic table, including the lanthanides. When the longest dimension of the nanoparticle is typically below about 10 nm, the nanoparticles may assemble in larger structures. Assembling of nanoparticles in larger structure may typically be triggered by interactions between nanoparticles and a biocompatible polymer(s), protein(s), etc. Larger structure may also be obtained by trapping the nanoparticles in a carrier, typically a plain carrier such as gelatin structure (also herein identified as "gelatin nanoparticle") or a hollow carrier such as liposome. After in vivo administration, those larger structures may further release the nanoparticles.

When inorganic and when the longest dimension of said nanoparticle is typically of at least 10 nm, typically between 10 and less than 100 nm, the nanoparticle may comprise at least one of, or may consist in (i) one or more divalent metallic elements selected for example from Mg, Ca, Ba and Sr, (ii) one or more trivalent metallic element selected for example from Fe and Al, and (iii) one or more tetravalent metallic element comprising Si.

In a particular embodiment, the inorganic material of the nanoparticle is selected from (i) one or more divalent metallic elements selected for example from Mg, Ca, Ba and Sr (ii) one or more trivalent metallic element selected for example from Fe and Al and (iii) one or more tetravalent metallic element comprising Si.

In a further particular embodiment, the inorganic material of the nanoparticle is selected from calcium carbonate ($CaCO_3$), magnesium carbonate ($MgCO_3$), magnesium hydroxide ($Mg(OH)_2$), iron hydroxide ($Fe(OH)_2$), iron oxyhydroxide ($FeOOH$), iron oxide ($Fe_3O_4$ or $Fe_2O_3$), aluminium oxide ($Al_3O_4$), aluminium hydroxide ($Al(OH)_3$), aluminium oxyhydroxide ($AlOOH$) and silicium oxide ($SiO_2$).

The nanoparticles used in the herein described compositions are to be biocompatible, i.e. compatible with living tissues. When required by their composition, the nanoparticles are thus to be coated with a biocompatible material to become usable. In a particular embodiment of the invention, the herein mentioned nanoparticle is thus covered with a biocompatible coating.

The biocompatible material can be an agent allowing interaction with a biological target. Such an agent will typically bring a positive or a negative charge on the nanoparticle's surface.

An agent forming a positive charge on the nanoparticle's surface can be for example selected from aminopropyltriethoxisilane and polylysine. An agent forming a negative charge on the nanoparticle surface can be for example selected from a phosphate (for example a polyphosphate, a metaphosphate, a pyrophosphate, etc.), a carboxylate (for example a citrate or dicarboxylic acid, in particular succinic acid) and a sulphate.

The nanoparticle can be coated with a biocompatible material selected from an agent displaying a steric group. Such a group may be selected for example from polyethylene glycol (PEG); polyethylenoxide; polyvinylalcohol; polyacrylate; polyacrylamide (poly(N-isopropylacrylamide)); polycarbamide; a biopolymer; a polysaccharide such as dextran, xylan, hyaluronic acid and cellulose; collagen; and a switterionic compound such as polysulfobetain.

The biocompatible coating may advantageously be a "full coating" (complete monolayer). This implies the presence of a very high density of biocompatible molecules creating an appropriate charge on the whole surface of the nanoparticle.

The biocompatible coating may further comprise a labelling agent known by the skilled person allowing the visualisation of the nanoparticles, for example a coloured agent which is detectable when using standard imaging equipment.

Anyone of the herein described nanoparticle can further be coated with an agent enhancing its recognition by specific cells, in particular by enterocytes and/or hepatocytes. Such an agent is typically a carbohydrate. When the biocompatible nanoparticle is to be administered through intravenous (IV) route, the agent enhancing the nanoparticle(s)' recognition by hepatocytes advantageously comprises, or consists in, saccharide(s) such as galactose, N-acetylgalactosamine, N-acetyl-glucosamine or a mixture thereof. When the biocompatible nanoparticle is to be administered through oral or enteral route, the agent enhancing the nanoparticle(s)' recognition by enterocytes and/or by hepatocytes advantageously comprises, or consists in, saccharide(s) such as a mannose, a lectin or a vitamin.

As the shape of the particle can influence its "biocompatibility", particles having a quite homogeneous shape are herein preferred. For pharmacokinetic reasons, nanoparticles being essentially spherical/round or ovoid in shape are thus preferred. Such a shape also favors the nanoparticle interaction with, or uptake by, cells. Spherical/round shape is particularly preferred.

In the spirit of the invention, the term "nanoparticle" refers to a product, in particular a synthetic product, with a size in the nanometer range, typically with a size of at least 4 nm and below 100 nm.

The terms "size of the nanoparticle", "largest size of the nanoparticle" and "longest size of the nanoparticle" herein typically refer to the "longest or largest dimension of the nanoparticle" or "diameter of the nanoparticle" when spherical/round or ovoid in shape. In a particular embodiment where the composition comprises a "first" and a "second" biocompatible nanoparticle, each of said nanoparticles comprising, or consisting in, at least one natural compound or a synthetic analog thereof, the longest dimension of "second" nanoparticle is preferably longer than the longest dimension of "first" nanoparticle. The ratio of the longest dimension of the "second" and of the "first" nanoparticle is typically equal to about 5, for example equal to about 4, 3, 2 and 1.5.

The size of the "first" and optionally "second" biocompatible nanoparticle is preferably of at least 4 nm and below 100 nm, for example between about 10 nm, 15 nm or 20 nm and about 90 or 95 nm.

Transmission Electron Microscopy (TEM) or Cryo-TEM can be used to measure the size of the nanoparticle. As well, Dynamic Light Scattering (DLS) can be used to measure the hydrodynamic diameter of nanoparticles in solution. These two methods may further be used one after each other to compare hydrodynamic diameter of nanoparticle measured by DLS and size of nanoparticles measured by TEM or Cryo-TEM, in order to confirm said size. A preferred method is DLS (Ref. International Standard IS022412 Particle Size Analysis—Dynamic Light Scattering, International Organisation for Standardisation (ISO) 2008).

The combined administration to a subject of the biocompatible nanoparticle(s) and of the compound(s) of interest, or of the pharmaceutical (i.e. therapeutic or prophylactic) composition of the invention, typically allows a reduction of at least about 20%, preferably at least about 25%, even more preferably at least about 30%, for example a reduction of at least about 40% of the dose(s) of the pharmaceutical compound(s) administered to a subject, when compared to the standard pharmaceutical dose(s) of said compound(s), for an equivalent bioavailability thereof in the subject. This advantageous effect is typically obtained when the at least one nanoparticle is administered to the subject in need of the compound of interest separately from said compound of interest, typically with an interval of between at least about 5 minutes and about 72 hours.

Different molecules or agents can be used according to the present teaching as the at least one compound of interest, typically as the at least one pharmaceutical compound of interest, which is administered in combination with the at least one biocompatible nanoparticle as described hereinabove. This compound is preferably selected from a therapeutic or a prophylactic compound as previously explained. In a particular embodiment, nanoparticle(s) are administered with several compounds of interest, typically with at least two compounds of interest.

Preferred pharmaceutical compounds of interest are compounds of poor bioavailability (i.e. compounds which undergone "first pass metabolism" or post-absorption immediate clearance) when administered to subject in need thereof. They are typically compounds which are substrates of human cytochrome P450 (CYP) enzymes. These compounds/substrates are typically catalyzed by or metabolized (i.e. physically and functionally degraded, for example cleaved or oxidized) by at least one enzyme selected from CYP1A1, CYP1A2, CYP1B1, CYP2A6, CYP2B6, CYP2C8, CYP2C9, CYP2C19, CYP2D6, CYP2E1 and CYP3A4, for example CYP1A1, CYP1A2, CYP1B1, CYP2A6, CYP2C8, CYP2C9, CYP2C19, CYP2D6, CYP2E1, CYP3A4, preferably from CYP1A2, CYP2A6, CYP2C9, CYP2C19, CYP2D6, CYP2E1, CYP3A4. Examples, among others [such as those identified in "Summary of information on human CYP enzymes": Human P450 metabolism data. Rendic S. Drug metabolism reviews, 34(1&2), 83-448 (2002); and in "Review of Therapeutics; Update: Clinically Significant Cytochromes P-450 drug interactions". Landrum Michalets E. Pharmacotherapy Volume 18 Number 1, 1998], of pharmaceutical compounds of interest are proton pump inhibitors (omeprazole, pantoprazole and rabeprazolc for instance), statins (fluvastatin, simvastatin, lovastatin and atorvastatin for instance), doxorubicin, docetaxel, etoposide, tamoxifen, warfarin, efavirenz, testosterone (testogel, androgel, axiron for instance), estrogen, progesterone, paclitaxel, rifampin, aprepitant, bortezomid, budesonide, buspirone, conivaptan, darifenacin, darunavir, dasatinib, dronedarone, eletriptan, eplerenone, everolimus, felodipine, imatinib, indinavir, fluticasone, lopinavir, lovastatin, lurasidone, maraviroc, midazolam, nilotinib, nisoldipine, quetiapine, saquinavir, sildenafil, simvastatin, sirolimus, tolvaptan, tipranavir, triazolam, vardenafil, atomoxetine, desipramine, dextromethorphan, metoprolol, nebivolol, perphenazine, tolterodine, venlafaxine, Alosetron, duloxetine, melatonin, ramelteon, tacrine, tizanidine, etc.

Examples of pharmaceutical compounds substrates of CYP1A2, CYP2D6 and CYP3A4 are listed in table 1 [examples of substances of interest, substrates of human CYP enzymes (Summary of information on human CYP enzymes: *Human P450 metabolism data*. Rendic S. Drug metabolism reviews, 34(1&2), 83-448 (2002))] and table 2 [Non-exhausting list of Cytochrome 3A4, 2D6 and 1A2 isoenzyme substrates (Review of Therapeutics; *Update: Clinically Significant Cytochromes P-450 drug interactions*. Landrum Michalets E. Pharmacotherapy Volume 18 Number 1, 1998); and www.FDA.gov].

TABLE 1

| Enzyme | Doxorubicin | Docetaxel | Tamoxifen | Warfarin | Efavirenz | Paclitaxel | Rifampin |
|---|---|---|---|---|---|---|---|
| CYP1A | | | Substrate | | | | |
| CYP1A1 | | | | Substrate | | | |
| CYP1A2 | | | | Substrate | | | |
| CYP1B1 | | Substrate inhibitor | inhibitor | | | | |
| CYP2A6 | | | Substrate | | | | |
| CYP2B6 | | | | | Substrate inhibitor | | inducer |
| CYP2C8 | | | inhibitor | Substrate | | | |
| CYP2C9 | | | | | inhibitor | | Inducer Inducer substrate |
| CYP2C18 | | | | Substrate | | | inducer |
| CYP2C19 | | | | | inhibitor | | |
| CYP2D6 | inhibitor | | substrate | | inhibitor | | |
| CYP2E1 | | | | | | | |
| CYP2F1 | | | | | | | |
| CYP3A4 | Substrate inhibitor | Substrate | Substrate | Substrate | Substrate Inducer Inhibitor | Substrate inhibitor | inducer |
| CYP3A5 | | | | | | | |
| CYP3A7 | | | | | | | |
| CYP4A11 | | | | | | | |
| CYP19 | | | Inhibitor | | | | |

TABLE 2

| CYP3A4 | CYP2D6 | CYP1A2 |
|---|---|---|
| doxorubicin<br>paclitaxel<br>aprepitant,<br>budesonide,<br>buspirone,<br>conivaptan,<br>darifenacin,<br>darunavir,<br>dasatinib,<br>dronedarone,<br>eletriptan,<br>eplerenone,<br>everolimus,<br>felodipine,<br>imatinib<br>indinavir,<br>fluticasone,<br>lopinavir,<br>lovastatin,<br>lurasidone,<br>maraviroc,<br>midazolam,<br>nilotinib<br>nisoldipine,<br>quetiapine,<br>saquinavir,<br>sildenafil,<br>simvastatin,<br>sirolimus,<br>tolvaptan,<br>tipranavir,<br>triazolam,<br>vardenafil | atomoxetine,<br>desipramine,<br>dextromethorphan,<br>metoprolol,<br>nebivolol,<br>perphenazine,<br>tolterodine,<br>venlafaxine | alosetron,<br>duloxetine,<br>melatonin,<br>ramelteon,<br>tacrine,<br>tizanidine |

Preferred substrates of CYP3A4 (i.e. compounds of interest which are metabolized by CYP3A4) are thus for example preferably selected from:

- a tyrosine kinase inhibitor for example selected from imatinib, nilotinib, sorafenib, crizotinib and sunitinib;
- a statin such as simvastatin, lovastatin or atorvastatin
- an EGFR inhibitors for example selected from erlotinib and lapatinib;
- a proteasome inhibitor such as bortezomib; and
- a cytotoxic such as etoposide, paclitaxel or docetaxel.

The combined administration of the biocompatible nanoparticle(s) together with the compound of interest as herein described maintains the pharmaceutical (i.e. therapeutic, prophylactic), typically therapeutic, benefit of the compound(s) of interest for an administered reduced dose, when compared to pharmaceutical benefit and toxicity induced by the standard pharmaceutical, typically therapeutic, dose of said compound(s).

The nanoparticles are advantageously cleared from the subject in need of the compound of interest to whom it has been administered typically within 1 hour and 6 weeks, for example 1 month (4 weeks), within 1 hour and 1 month, for example between 1 hour and 3 weeks, between 1 hour and 2 weeks, or between 1 hour and 1 week, following its administration to the subject.

The material constituting the nanoparticle (including its biocompatible coating when present) is important in determining the biopersistence of the nanoparticle. The nanoparticle may be regarded as biodegradable (when constituted for example by a biodegradable polymer such as PLGA or PLA), dissolvable (iron oxide for example) or non-biodegradable and non-dissolvable. Biodegradable and dissolvable nanoparticles facilitate rapid nanoparticle clearance from the subject.

The pharmaceutical compositions of the invention can be used for preventing or treating a cardiovascular disease, a Central Nervous System (CNS) disease, a gastrointestinal disease, a genetic disorder, a hematological disorder, a hormonal disorder, an immune disorder, an infectious disease, a metabolic disorder, a musculoskeletal disorder, a cancer, a respiratory disease, an intoxication, etc. In a preferred embodiment, the pharmaceutical composition is used in the context of a cardiovascular disease, a CNS disease, a cancer, an infectious disease or a metabolic disorder.

The pharmaceutical compositions of the invention can be used for preventing or treating a cardiovascular disease, a Central Nervous System (CNS) disease, a gastrointestinal disease, a genetic disorder, an hematological disorder, a hormonal disorder, an immune disorder, an infectious disease, a metabolic disorder, a musculo skeletal disorder, a cancer, a respiratory disease, an intoxication, etc. In a preferred embodiment, the pharmaceutical composition is used in the context of a cardiovascular disease, a CNS disease, a cancer, an infectious disease or a metabolic disorder.

Also herein described is a method for treating a subject suffering of a disease such as those herein mentioned, wherein said method comprises administering to said subject a pharmaceutical composition of the invention, typically at least one biocompatible nanoparticle(s) and at least one compound of interest as herein described. Administration of any of said at least one nanoparticle or of said at least one compound of interest can be a single administration of each, repeated administrations of each, for example several consecutive administrations of each. The at least one biocompatible nanoparticle may be administered once and the at least one compound of interest may be administered more than once and vice versa.

The following examples illustrate the invention without limiting its scope.

a. nanoparticle of furanocoumarin
b. furanocoumarin nanoparticle entrapped in a plain nanoparticle (organic or inorganic; possibly conjugated)
c. furanocoumarins dispersed in a plain nanoparticle (organic or inorganic)
d. furanocoumarins entrapped in the aqueous cavity of hollow nanoparticle
e. furanocoumarins entrapped in the layer of hollow nanoparticle
f. furanocoumarins adsorbed or conjugated on the surface of a plain nanoparticle (organic or inorganic) or hollow nanoparticle (the conjugation could be performed directly between surface and furanocoumarin or via a linker of different size).

Figure 6:
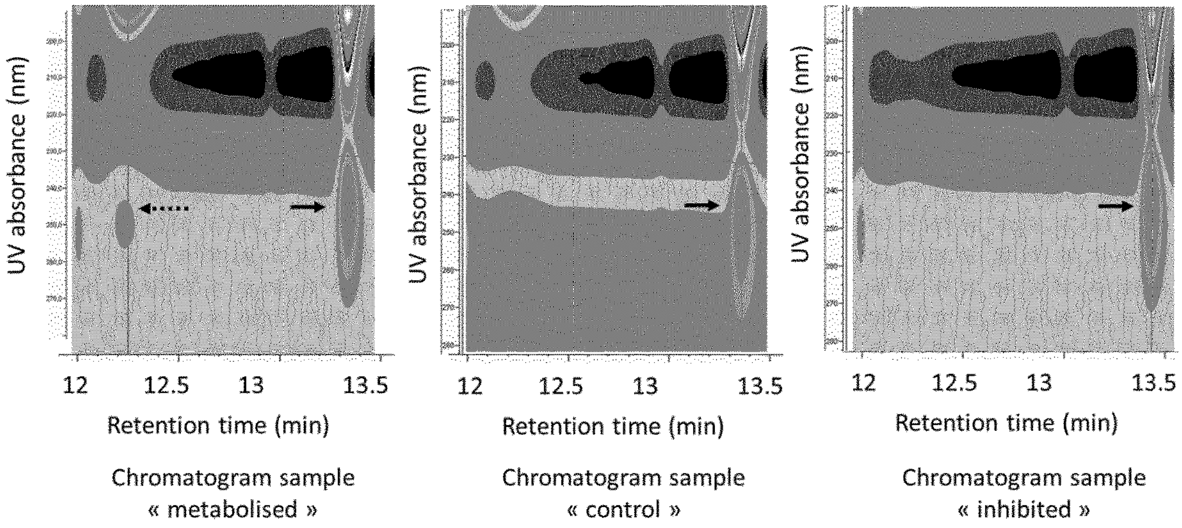

FIG. 6: 3D chromatogram outputs of HPLC-UV injection of "control" sample (docetaxel), "metabolized" sample (HepaRG cells treated with docetaxel) and "inhibited" sample (HepaRG cells treated sequentially with DHB micelles (example 6) and docetaxel).

In the "control" sample chromatogram, the black arrow corresponds to the docetaxel peak;

In the "inhibited" sample chromatogram, the black arrow corresponds to the docetaxel peak;

In the "metabolized" sample chromatogram, the dotted arrow (retention time 12.25 minutes) corresponds to a metabolite of docetaxel and the black arrow corresponds to docetaxel peak.

Figure 7:
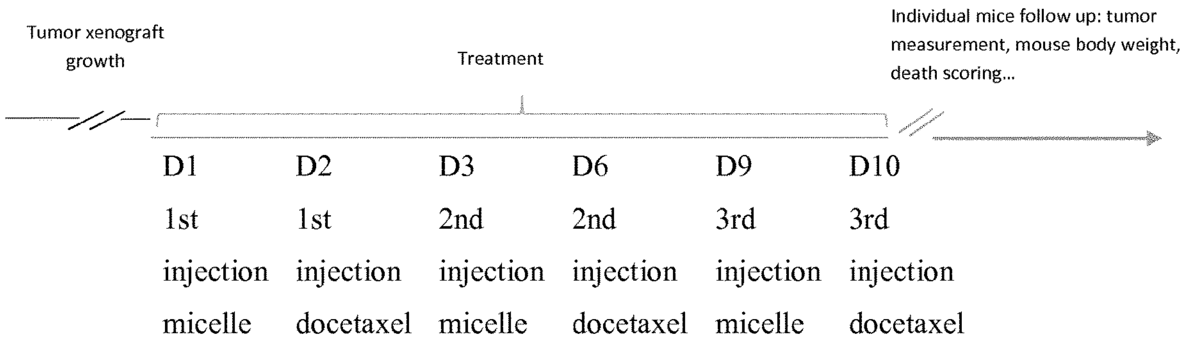

FIG. 7: Schedule of administration of the biocompatible nanoparticles (DHB micelles) and docetaxel in HT-29 tumor model xenografted on MRI nude mice.

Figure 8:
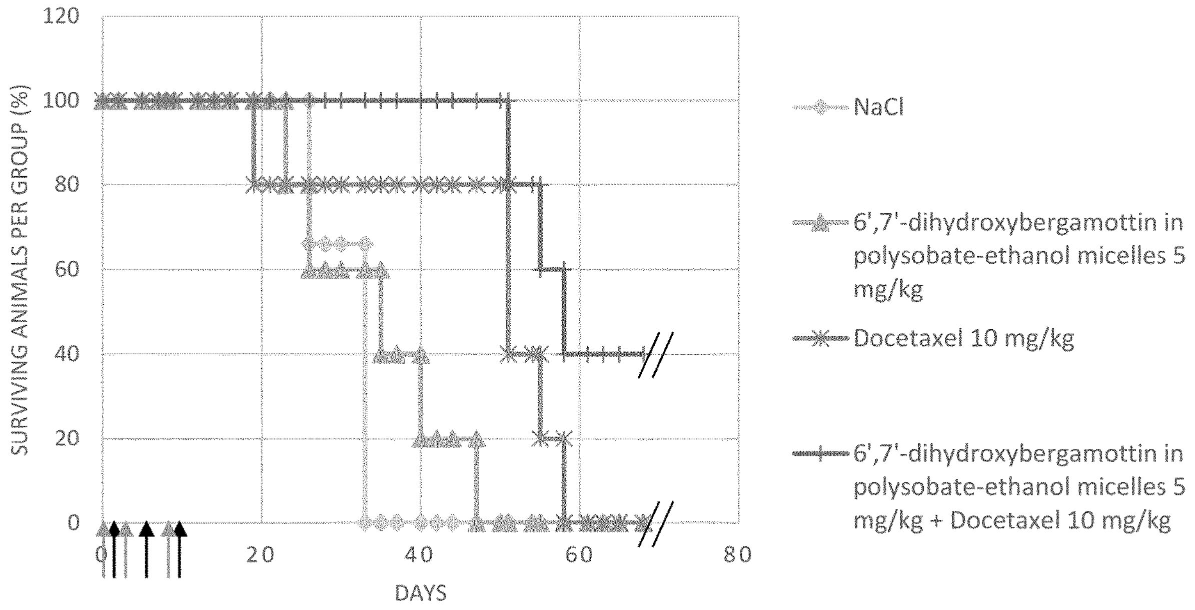

FIG. 8: Kaplan-Meier curves for group 1 (control group: NaCl), group 2 (control group: DHB micelles 0.93 g/L, 5 mg/kg), group 3 (treatment group: docetaxel 2 g/L, 10 mg/kg) and group 4 (treatment group: pharmaceutical composition comprising (i) DHB micelles 0.93 g/L, 5 mg/kg injected 24 hrs before (ii) Docetaxel 2 g/L, 10 mg/kg):

Group 1: Aqueous saline (NaCl 0.9%) on D1, D2, D3, D6, D9, D10;

Group 2: DHB micelles on D1, D3, D9;

Group 3: Docetaxel (2 g/L) 10 mg/kg on D2, D6, D10;

Group 4: (i) DHB micelles (0.93 g/L) 5 mg/kg on D1, D3, D9 and (ii) Docetaxel (2 g/L) 10 mg/kg on D2, D6, D10.

Arrows: injections (clear arrow DHB micelles and dark arrow docetaxel).

EXAMPLES

Example 1

Preparation of Nanoparticles (or Nanocrystals) Consisting in Furanocoumarin (Such as Bergamottin, DHB, 6',7'-Epoxybergamottin and/or Paradisin)

There are various options to produce nanoparticles in the desired shape and size [Nanocrystal technology, drug delivery and clinical applications. Junghanns J-U A H, Müller R H. International Journal ofNanomedicine, 2008:3(3) 295-309].

Basically three principles can be used: precipitation methods, milling methods and homogenization methods, as well as any combination thereof.

Precipitation Methods:

Furanocoumarins are dissolved in a solvent and subsequently added to a non solvent, leading to a precipitation of finely dispersed furanocoumarin nanoparticles. Alternatively, furanocoumarin may be added directly into water, possibly in the context of a ultrasound treatment, and self-assembling is driven by hydrophobic interactions.

Milling Methods:

Milling media (such as ball mills), furanocoumarins and dispersion medium (such as water) are charged into a milling chamber. Shear forces of impact, generated by the movement of the milling media, lead to particle size reduction.

Homogenization Methods:

Typically this method requires microfluidizer technology which can generate small particles by frontal collision of two fluid streams under pressures up to 1700 bars. Of note, supercritical fluid methods may also be employed to generate nanoparticles.

Example 2

Figure 1:
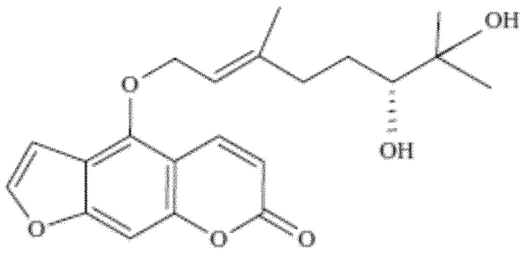
FIG. 1: Furanocoumarin.
Figure 1:
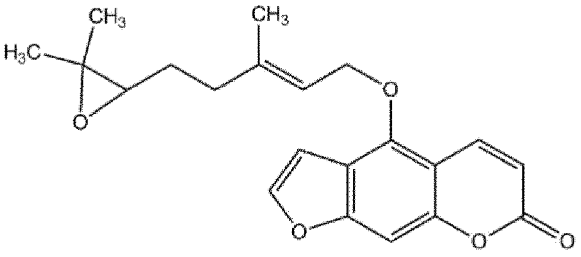
Figure 1:
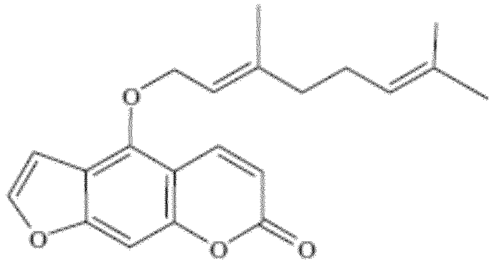
Figure 1:
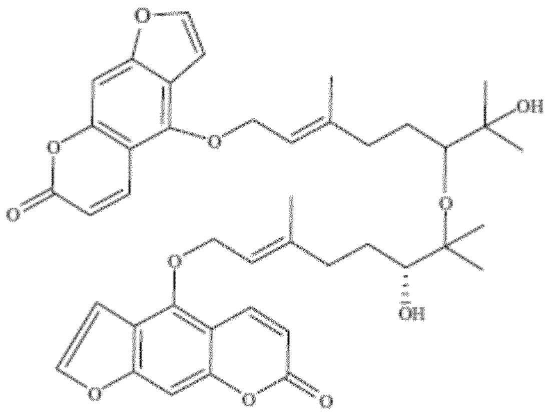
Figure 2:
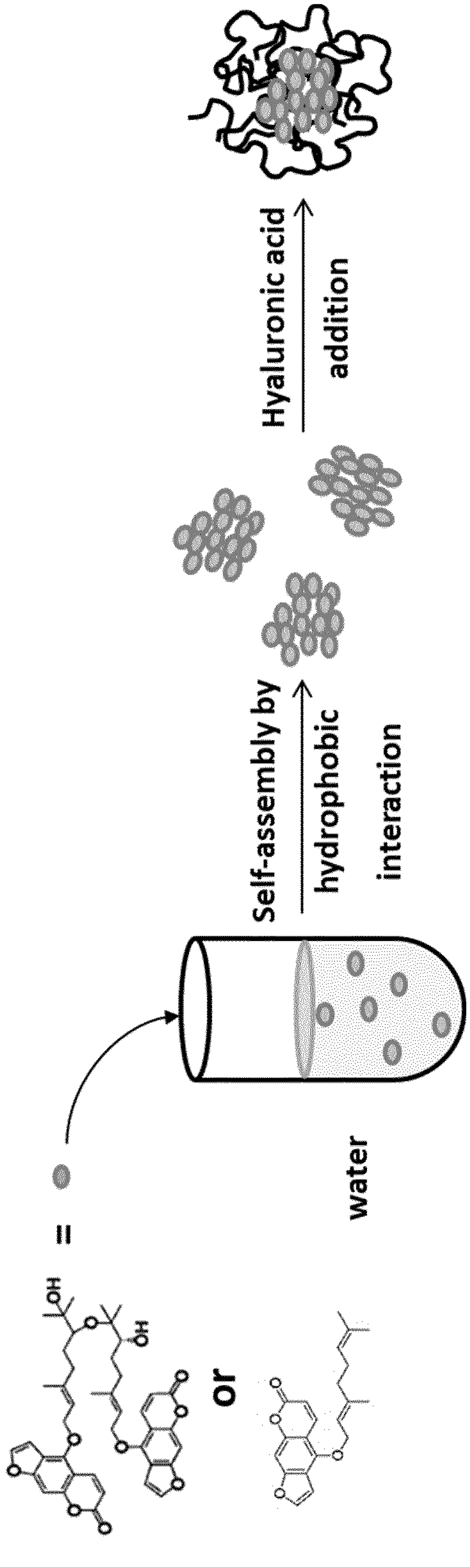
FIG. 2: Schematic synthesis of hyaluronan coated nanoparticles consisting in furanocoumarin (such as bergamottin, DHB, 6',7'-epoxybergamottin, paradisin, etc.) by self-assembly in water (cf. example 2).

Preparation of Hyaluronan Coated Nanoparticles Consisting in Furanocoumarin by Self-Assembly in Water (cf. FIG. 2)

Nanoparticles consisting in furanocoumarin are typically obtained by direct addition of furanocoumarins (such as bergamottin, DHB, 6',7'-epoxybergamottin and/or paradisin) in water, the mixture being then submitted to an ultrasonication treatment. Hyaluronic acid polymers are subsequently added to the obtained suspension. A polymeric layer of hyaluronic acid is formed onto the nanoparticles' surface.

Example 3

Figure 3:
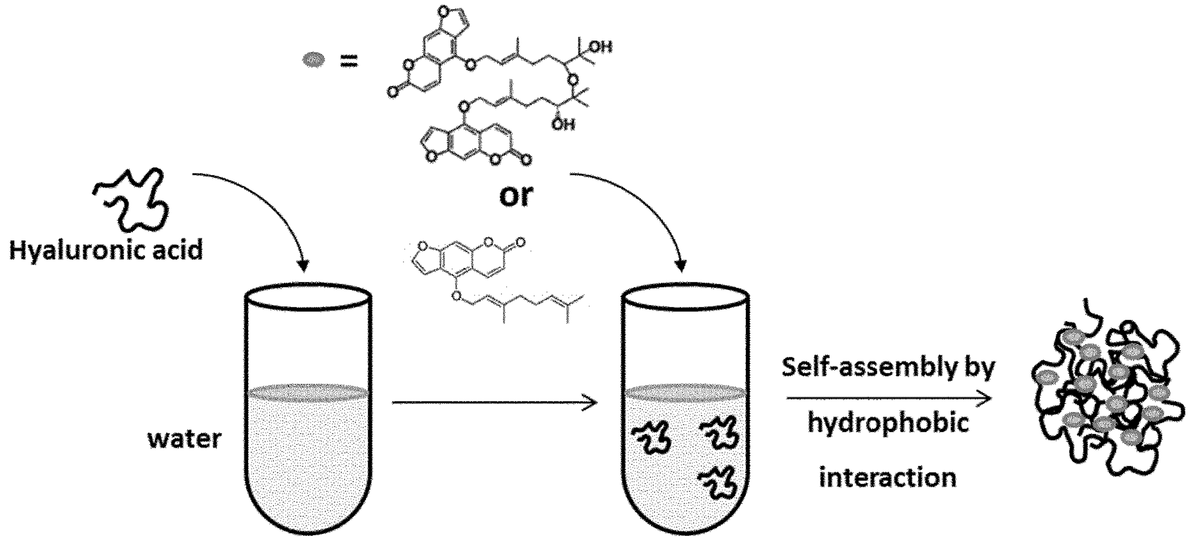
FIG. 3: Schematic synthesis of hyaluronan coated nanoparticles consisting in furanocoumarin (such as bergamottin, DHB, 6',7'-epoxybergamottin, paradisin, etc.) by self-assembly in water (cf. example 3).

Preparation of Hyaluronan Coated Nanoparticles Consisting in Furanocoumarin by Self-Assembly in Water (cf. FIG. 3)

Hyaluronic acid polymers are first dissolved in water. Subsequently furanocoumarins (such as bergamottin, DHB, 6',7'-epoxybergamottin and/or paradisin) are added to the solution, said solution being then submitted to a ultrasonication treatment. A polymeric layer of hyaluronic acid is formed onto the nanoparticles' surface.

Example 4

Figure 4:
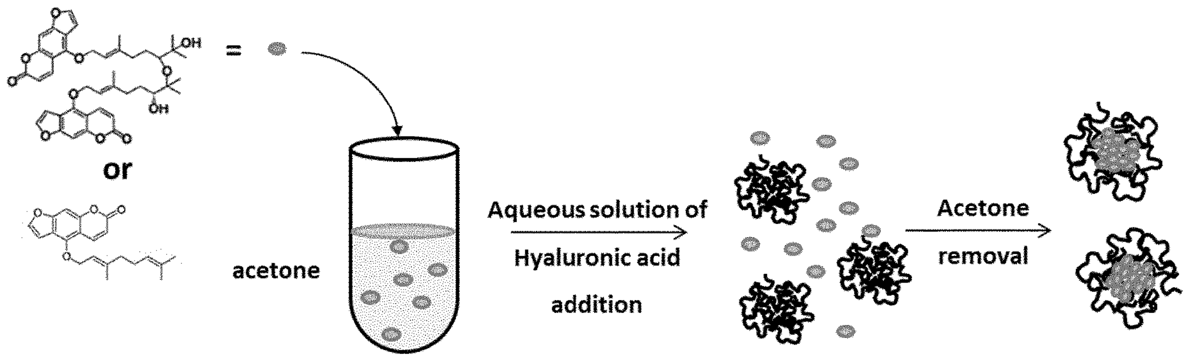
FIG. 4: Schematic synthesis of hyaluronan coated nanoparticles consisting in furanocoumarin (such as bergamottin, DHB, 6',7'-epoxybergamottin, paradisin, etc.) by solvent removal (cf. example 4).
Figure 5:
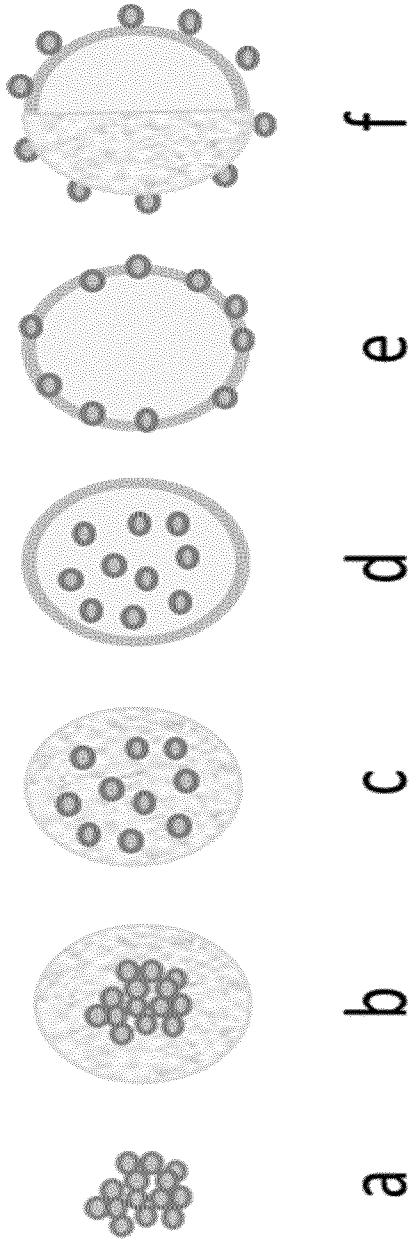
FIG. 5: Schematic representation of nanoparticles consisting in, or comprising furanocoumarin.

Preparation of Hyaluronan Coated Nanoparticles Consisting in Furanocoumarin by Solvent Removal (cf. FIG. 4)

Furanocoumarins (such as bergamottin, DHB, 6',7'-epoxybergamottin and/or paradisin) are added to a solution of acetone. Hyaluronic acid polymers dissolved in water are subsequently added to the furanocoumarins' solution. Acetone is removed by evaporation above 65° C. A polymeric layer of hyaluronic acid is formed onto the furanocoumarin nanoparticles' surface.

Of note, in the above examples 2, 3 and 4, the hyaluronic acid polymer can be further cross-linked in water.

Of note, in the above examples 2, 3 and 4, chitosan polymers, PLGA-hyaluronic acid copolymers, PLGA-PEG copolymers, or any water soluble polymer or co-polymer as described herein above can replace partially or totally hyaluronic acid polymer.

Of note, in the above examples 2, 3 and 4 the polymer can be formally conjugated with furanocoumarin monomer or dimer.

Example 5

Furanocoumarins Inhibit Human CYP Enzymes

The below Table 3 summarizes the role of furanocoumarms and of other natural compounds of interest or synthetic analog thereof as inhibitors of human CYP enzymes (cf. Summary of information on human CYP enzymes: Human P450 metabolism data. Rendic S. Drug metabolism reviews, 34(1 & 2), 83-448 (2002)):

| Enzyme | furanocoumarin | Flavonoid Acacetin | Flavonoid Naringenin | Vitamin A retinol | Flavonoid Apigenin | Flavonoid Quercetin | Fatty acid Arachidonic acid |
|---|---|---|---|---|---|---|---|
| CYP1A | | Inhibitor | | | | | |
| CYP1A1 | | | | Inhibitor | Inhibitor | Inhibitor | Inhibitor |
| CYP1A2 | Inhibitor: DHB, Bergamottin Furanocoumarin extracts | | | | Inhibitor | Inhibitor | Substrate Inhibitor |
| CYP1B1 | | | Inhibitor | | | | Inhibitor |
| CYP2A6 | Inhibitor: Bergamottin | | | | | | Substrate |
| CYP2B6 | | | | Inhibitor | | | |
| CYP2C8 | | | | Inhibitor Substrate | | Inhibitor | Substrate |
| CYP2C9 | Inhibitor: Bergamottin Furanocoumarin extracts | | | | | | Inhibitor Substrate |
| CYP2C18 | | | | | | | |
| CYP2C19 | Inhibitor: Bergamottin | | | | | | Substrate |
| CYP2D6 | Inhibitor: Bergamottin Furanocoumarin extracts | | | Substrate | | | Inhibitor |
| CYP2E1 | Inhibitor: Bergamottin | | | | | | Inhibitor |
| CYP2F1 | | | | | | | |
| CYP3A4 | Inhibitor: Bergamottin Furanocoumarin dimers, extracts or trimers | | inhibitor | | | Inhibitor | Inhibitor Substrate |
| CYP3A5 | | | | | | | |
| CYP3A7 | | | | | | | |
| CYP4A11 | | | | | | | Substrate |
| CYP4B1 | | | | | | | Substrate |
| CYP4F2 | | | | | | | Substrate |
| CYP4F8 | | | | | | | Substrate |
| CYP4F12 | | | | | | | Substrate |
| CYP11B1 | | | Inhibitor | | | Inhibitor | |
| CYP19 | | | Inhibitor | | | Inhibitor | |

Furanocoumarins inhibit in particular the following human CYP enzymes: CYP1A2, CYP2A6, CYP2C9, CYP2C19, CYP2D6, CYP2E1 and CYP3A4.

Example 6

Synthesis and Characterization of Micelles Encapsulating 6'-, 7'-Dihydroxybergamottin (DHB) (i.e. DHB Micelles=Biocompatible Nanoparticle as Defined herein Above in the Detailed Description)

Micelles of 6', 7'-dihydroxybergamottin (DHB) (i.e. DHB micelles) were formed by self-assembly, by dissolving a surfactant-ethanol solution in aqueous solution. The surfactant (Polysorbate 80) and anhydrous ethanol were mixed 1:1 (v/v) to form a polysorbate 80-ethanol solution.

DHB was then weighted and dissolved in the polysorbate 80-ethanol (1:1, v/v) solution to a concentration up to the solubility limit. Fifteen (15) minutes of strong vortexing were subsequently performed to completely dissolve the DHB powder.

Once the dissolution of DHB was completed, micelles were formed by addition of an aqueous solution (either water of saline water) to the polysorbate 80-ethanol (1:1, v/v) solution containing DHB. Typically, saline water containing NaCl 1% (w/w) was added to the polysorbate 80-ethanol solution containing DHB in a ratio equal to 10:1 (saline water: polysorbate 80-ethanol, v:v). Under these conditions, the resulting final concentration of DHB in micelles solution was 2.5 mM.

a) Particle Size Characterization:

DHB micelles in saline water (1% w/w NaCl) were measured by dynamic light scattering. The hydrodynamic diameter of micelles was equal to 11.6 nm (distribution by intensity) with a polydispersity index (PdI) equal to 0.089.

b) In Vitro Cytochromes P450 Inhibition of Pharmaceutical Compound (Here Docetaxel) by DHB Micelles "Control" Sample: Docetaxel 1 μM A "control" sample corresponding to docetaxel 1 μM was used for high-performance liquid chromatography (HPLC) measurement. Docetaxel powder was dissolved in polysorbate 80-ethanol (1:1, v:v) solution. Saline water was subsequently added in a ratio 1:9 (polysorbate 80-ethanol:saline water, v:v). The obtained suspension was diluted in cell culture down to a concentration of docetaxel of 1 μM. Then, the incubation medium was collected and acetonitrile was added to the medium to precipitate proteins (1:1 v/v).

"Metabolised" Sample: Incubation on HepaRG Cells of Docetaxel 1 μM-4 hrs

Docetaxel powder was dissolved in polysorbate 80-ethanol (1:1, v:v) solution. Saline water was subsequently added in a ratio 1:9 (polysorbate 80-ethanol:saline water, v:v). The obtained suspension was incubated at the nontoxic concentration of 1 μM for 4 hours on induced HepaRG cells (HepaRG is human hepatic cell-line of hepatocyte progenitors, cultured and induced according to the manufacturer's protocol). Then, the incubation medium was collected and acetonitrile was added to the medium to precipitate proteins (1:1 v/v).

"Inhibited" Sample: Sequential Incubation on HepaRG Cells of (1) DHB Micelles 10 μM-1 h and (2) Docetaxel 1 μM-4 hs Polysorbate 80-ethanol micelles loaded with 6', 7'-dihydroxybergamottin (i.e. DHB micelles) 10 μM were incubated 1 hour on induced HepaRG cells. Then, cells were rinsed with PBS and incubated with the pharmaceutical compound of interest (here docetaxel known to be a substrate of CYP3A4). Docetaxel was incubated at nontoxic concentration of 1 μM for 4 hours. Then, the incubation medium was collected and acetonitrile was added to the medium to precipitate proteins (1:1 v/v).

The 3 Samples ("control", "metabolized", and "inhibited" samples) were vortexed for 30 seconds and centrifuged at 3000 g for 30 minutes. Their supernatants were mixed with ethyl acetate (1:1 v/v) to separate the organic phase from the aqueous phase. The organic phases of each supernatant were dried out in a Rotavapor at 60° C. and re-suspended in methanol. The resulting methanol solutions were injected in the HPLC-UV (Thermo Fisher Scientific Inc.) with an auto-injector. 20 μL of sample were separated on a C18 3 μm, 150 mm×4.6 mm column (Advanced Chromatography Technologies Ltd.) in a gradient of eluent starting at 30% acetonitrile and 70% acidic water (0.1% formic acid), up to 100% acetonitrile in 25 minutes. The chromatograms obtained were extracted at an UV emission wavelength of 230 nm.

FIG. 6 shows that the sequential treatment of DHB micelles and docetaxel compound on HepaRG cells (i.e. treatment of DHB micelles lh before the treatment of docetaxel) inhibits the metabolization of docetaxel; i.e. the peak corresponding to docetaxel metabolite is no longer present when cells are treated with the sequential administration of DHB micelles and docetaxel when compared to cells treated with docetaxel alone.

c) In Vivo Cytochromes P450 Inhibition of Pharmaceutical Compounds by DHB Micelles This study was performed to investigate the efficacy of the pharmaceutical composition comprising the combination of (i) the DHB micelles (biocompatible nanoparticles) and of (ii) docetaxel as the pharmaceutical compound of interest, in HT-29 tumor model xenografted on NMRI nude mice.

The human colorectal adenocarcinoma HT-29 cell line was purchased at the ATCC. The cells were cultured in McCoy's 5a Medium supplemented with 10% fetal bovine serum. NMRI female nude mice (NMRI-Foxlnu/Foxnlnu) 6-7 weeks were ordered from Janvier Labs (France). Mice were xenografted with HT-29 cells: 5 million cells were injected in 50 μL subcutaneously in the lower right flank. Tumor volume in $mm^3$ was measured with a digital caliper, calculated with the formula:

$$\text{Tumor volume } (mm^3) = \frac{\text{length } (mm) \times \text{width}^2\ (mm^2)}{2}.$$

Mice were randomised into separate cages and identified by a number (pawn tattoo) 2 weeks post xenograft, when the mean tumor volume reached 90 $mm^3$ (standard deviation 25%). Groups were made of 5 mice [except for the control aqueous saline (NaCl 0.9%) group, 3 mice] (see FIG. 7 for the schedule of administration):

Group 1: NaCl (control group). 3 mice were injected with saline water (NaCl 0.9%) intravenously in the tail vein, on D1 (day 1, corresponding to the first day of treatment), D2, D3, D6, D9, D10.

Group 2: 6', 7'-dihydroxybergamottin in polysorbate 80-ethanol micelles (DHB micelles) (control group). DHB micelles in saline water (NaCl 1% w:w) at 2.5 mM (0.93 g/L) were injected at a dose of 5 mg/kg intravenously in the tail vein, on D1, D3 and D9.

Group 3: Docetaxel 10 mg/kg (treatment group). Docetaxel (docetaxel anhydrous, Sigma Aldrich, European pharmacopeia) was dissolved in polysorbate 80-ethanol 1:1 (v/v) at 20 g/L. Prior to injection, saline water (NaCl 1 % w:w) was added to polysorbate 80-ethanol solution containing the docetaxel compound down to concentration of docetaxel of 2 g/L. The resulting docetaxel suspension was administered intravenously through the tail vein at a dose of 10 mg/kg, on D2, D6 and D10.

Group 4: sequential administration of DHB micelles and Docetaxel 10 mg/kg (pharmaceutical composition group). Group 4 was treated as follows:

Intravenous injection through the tail vein of DHB micelles 2.5 mM at a dose of 5 mg/kg on D1, D3 and D9;

Intravenous injection through the tail vein of docetaxel suspension prepared as in group 3 herein above (2 g/L), at a dose of 10 mg/kg on D2, D6 and D10.

Mice were followed up for clinical signs, body weight and tumor size at least twice a week. The tumor volume was estimated from two-dimensional tumor volume measurements with a digital caliper using the following formula:

$$\text{Tumor volume (mm}^3\text{)} = \frac{\text{length (mm)} \times \text{width}^2\ (\text{mm}^2)}{2}$$

The overall survival of all animals was followed using the Kaplan-Meyer curves. As illustrated in FIG. 8, 40% of animals in the group treated by the pharmaceutical composition (group 4) survive for at least 15 days more than the group treated by docetaxel 10 mg/kg alone (group 3).

These results showed an advantageous overall survival when using the pharmaceutical composition of the present invention, when compared to docetaxel alone.

Example 7

Synthesis of Micelles Encapsulating Bergamottin (Bergamottin Micelles)

Micelles of bergamottin (i.e. Bergamottin micelles) were formed by self-assembly, by dissolving a surfactant-ethanol solution in aqueous solution. The surfactant (Polysorbate 80) and anhydrous ethanol are mixed 1:1 (v/v) to form a surfactant-ethanol solution.

Bergamottin was then weighted and dissolved in the polysorbate 80-ethanol (1:1, v/v) solution to a concentration up to the solubility limit. Fifteen (15) minutes of strong vortexing were subsequently performed to completely dissolve the bergamottin powder.

Once the dissolution of bergamottin was completed, micelles were formed by addition of an aqueous solution (either water of saline water) to the polysorbate 80-ethanol (1:1, v/v) solution containing bergamottin. Typically, saline water containing NaCl 1% (w/w) was added to the polysorbate 80-ethanol solution containing bergamottin in a ratio equal to 10:1 (saline water:polysorbate 80-ethanol, v:v). Under these conditions, the resulting final concentration of bergamottin in micelles solution was 2.5 mM.

Particle Size Characterization:

Bergamottin micelles in saline solution (1% w/w NaCl) were measured by dynamic light scattering. The hydrodynamic diameter of micelles was equal to 13.26 nm (distribution by intensity) with a polydispersity index (PdI) equal to 0.108.

Example 8

Synthesis of Hyaluronic Acid (HA) Nanoparticles Cross-Linked with 1-Ethyl-3-(3-Dimethylaminopropyl) Carbodiimide (EDC) and N-Hydroxysuccinimide (NHS), comprising 6', 7'-Dihydroxybergamottin (DHB)

Aqueous solution of HA polymer was prepared by mixing HA polymer in water (2.5 g/L, 5.4 mL) in a 100 mL beaker. Then, 17.0 mL of acetone was added to the flask and stirred with a mechanical agitation for 20 minutes (320 rpm). 0.125 mL of a solution of EDC (50 mg/mL) in water was added to the flask, followed 5 min later by an addition of 0.35 mL of a solution of NHS (27.5 mg/mL) in water. After mixing the solution for 5 min, 21.5 mL of acetone with 0.125 mL of DHB in acetone (10 g/L) were added to the solution and stirring was continued for 15 h30 (HA concentration ~0.30 g/L). Then, the reaction was stopped by dialysis of the solution against reverse osmosis water using dialysis membrane (Regenerated Cellulose (RC), MWCO 12-14 kDa) (minimum 2×4 hrs).

Particles Size Characterization

Nanoparticles hydrodynamic diameter was measured by DLS (hydrodynamic diameter (distribution by intensity)=92 nm in NaCl (150 mM) and PdI=0.148). Finally, the nanoparticles solution was concentrated with an Amicon® system (Biomax®; 50 kDa; d=25 mm; PES) and stored at 4° C. (Final HA concentration ~4.00 g/L).

Example 9

Synthesis of Hyaluronic Acid (HA)—Ethylenediamine (EDA) Nanoparticles Cross-Linked with 1 Ethyl-3-(3-Dimethylaminopropyl) Carbodiimide (EDC) and N-Hydroxysuccinimide (NHS), comprising 6', 7'-Dihydroxybergamottin (DHB)

Aqueous solution of HA polymer was prepared by mixing HA polymer in water (2.5 g/L, 5.3 mL) in a 100 mL beaker. Then, 17 mL of acetone was added to the flask and stirred with a mechanical agitation for 34 minutes (320 rpm). 0.125 mL of a solution of EDC (50 mg/mL) in water was added to the flask, followed 5 min later by 0.35 mL of a solution of NHS (27.5 mg/mL) in water and 0.125 mL of a solution of EDA (15 mg/mL) in water. After mixing the solution for 15 min, 21.5 mL of acetone with 0.180 mL of DHB (10 g/L) in acetone were added to the solution and stirring was continued for 20 min (HA concentration 0.30 g/L). Then, the reaction was stopped by dialysis of the solution against reverse osmosis water using dialysis membrane (Regenerated Cellulose (RC), MWCO 12-14 kDa) (minimum 2*4 h).

Particle Size Characterization

Nanoparticles hydrodynamic diameter was measured by DLS (hydrodynamic diameter (distribution by intensity)=95 nm in NaCl (150 mM) and PdI=0.136). Finally, the nanoparticles solution was concentrated with an Amicon® system (Biomax®; 50 kDa; d=25 mm; PES) and stored at 4° C. (Final HA concentration ~4.00 g/L).

The invention claimed is:

1. A therapeutic or prophylactic method comprising a step of administering at least one pharmaceutical compound to a subject in need thereof and a distinct step of administering at least one biocompatible nanoparticle to said subject, wherein the at least one biocompatible nanoparticle comprises bergamottin, 6',7'-dihydroxybergamottin (DHB) or a mixture thereof, the longest dimension of said at least one biocompatible nanoparticle is at least 4 nm and less than 100 nm, the at least one biocompatible nanoparticle is not used as the therapeutic or prophylactic compound, wherein the at least one pharmaceutical compound is a substrate of the human CYP3A4 and/or CYP2B6 enzymes, and wherein said at least one biocompatible nanoparticle is administered separately to the subject between 5 minutes and about 72 hours before the at least one pharmaceutical compound, the at least one biocompatible nanoparticle and the at least one pharmaceutical compound being both administered to the subject through an intravenous (IV) injection route.

2. The method according to claim 1, wherein the administration of the biocompatible nanoparticle(s) and of the at least one pharmaceutical compound allows a reduction of at least 20% of the administered at least one pharmaceutical compound therapeutic dose when compared to the standard therapeutic dose of said at least one pharmaceutical compound while maintaining the same bioavailability.

3. The method according to claim 1, wherein the at least one nanoparticle is cleared from the subject to whom it has been administered within a period of one hour and six weeks after its administration to a subject in need of the at least one pharmaceutical compound.

4. The method according to claim 1, wherein said at least one pharmaceutical compound is selected from docetaxel, doxorubicin, paclitaxel, aprepitant, budesonide, buspirone, conivaptan, darifenacin, darunavir, dasatinib, dronedarone, eletriptan, eplerenone, everolimus, imatinib, indinavir, fluticasone, lopinavir, lurasidone, maraviroc, midazolam, nilotinib, nisoldipine, quetiapine, saquinavir, sildenafil, simvastatin, sirolimus, tolvaptan, tipranavir, triazolam, vardenafil and efavirenz.

5. The method according to claim 1, wherein said at least one pharmaceutical compound is docetaxel or paclitaxel.

6. The method according to claim 5, wherein said at least one pharmaceutical compound is docetaxel.

7. The method according to claim 5, wherein said at least one pharmaceutical compound is paclitaxel.

8. The method according to claim 1, wherein the at least one biocompatible nanoparticle comprises bergamottin.

9. The method according to claim 1, wherein the at least one biocompatible nanoparticle comprises 6',7'-dihydroxybergamottin (DHB).

10. The method according to claim 1, wherein the at least one biocompatible nanoparticle comprises a mixture of bergamottin and 6',7'-dihydroxybergamottin (DHB).

11. The method according to claim 1, wherein the at least one biocompatible nanoparticle further comprises retinol.

12. A therapeutic or prophylactic method comprising a step of administering at least one pharmaceutical compound to a subject in need thereof and a distinct step of administering at least one biocompatible nanoparticle to said subject, wherein the at least one biocompatible nanoparticle comprises bergamottin, 6',7'-dihydroxybergamottin (DHB) or a mixture thereof, the longest dimension of said at least one biocompatible nanoparticle is at least 4 nm and less than 100 nm, the at least one biocompatible nanoparticle is not used as the therapeutic or prophylactic compound, wherein the least one pharmaceutical compound is a substrate of the human CYP3A4 and/or CYP2B6 enzymes, and wherein said at least one biocompatible nanoparticle is administered separately to the subject between 5 minutes and about 72 hours before the at least one pharmaceutical compound, the at least one biocompatible nanoparticle and the at least one pharmaceutical compound being both administered to the subject through an intravenous (IV) injection route, and wherein the method further comprises a step of administering a second biocompatible nanoparticle comprising at least one natural compound which is an inhibitor of a human CYP enzyme, the longest dimension of the second biocompatible nanoparticle being of at least 4 nm and less than 100 nm, and wherein the at least one (first) and/or second biocompatible nanoparticle(s) comprise(s) an agent enhancing nanoparticle(s)' recognition by enterocytes and/or by hepatocytes.

13. The method according to claim 12, wherein the at least one (first) and/or the second biocompatible nanoparticle comprises at least one inhibitor of a human CYP enzyme and said inhibitor is encapsulated in, trapped in, absorbed in, adsorbed on, linked on, conjugated to, attached to or bound to the at least one and/or to the second nanoparticle.

14. The method according to claim 12, wherein the first and second biocompatible nanoparticles are administered separately in an additional distinct step, or simultaneously, in a subject in need of the at least one pharmaceutical compound, and before said at least one pharmaceutical compound.

15. The method according to claim 12, wherein each of the at least one (first) and/or second biocompatible nanoparticles is further covered with a biocompatible coating.

16. The method according to claim 12, wherein the agent enhancing the nanoparticle(s)' recognition by hepatocytes comprises a saccharide.

17. The method according to claim 12, wherein the at least one biocompatible nanoparticle comprises bergamottin.

18. The method according to claim 12, wherein the at least one biocompatible nanoparticle comprises 6',7'-dihydroxybergamottin (DHB).

19. The method according to claim 12, wherein the at least one biocompatible nanoparticle comprises a mixture of bergamottin and 6',7'-dihydroxybergamottin (DHB).

* * * * *

UNITED STATES PATENT AND TRADEMARK OFFICE

CERTIFICATE OF CORRECTION

PATENT NO. : 11,304,902 B2
APPLICATION NO. : 15/529097
DATED : April 19, 2022
INVENTOR(S) : Agnès Pottier et al.

It is certified that error appears in the above-identified patent and that said Letters Patent is hereby corrected as shown below:

In the Specification

Column 18,
Line 49, "concentration 0.30" should read --concentration ~0.30--.

Signed and Sealed this
Twenty-fourth Day of January, 2023

Katherine Kelly Vidal

Katherine Kelly Vidal
*Director of the United States Patent and Trademark Office*